(12) United States Patent
Barbour et al.

(10) Patent No.: US 6,617,441 B1
(45) Date of Patent: Sep. 9, 2003

(54) DIAGNOSTIC TEST FOR BORRELIA INFECTION

(75) Inventors: Alan G. Barbour, San Antonio, TX (US); Carol Carter, Bulverde, TX (US)

(73) Assignee: Board of Regents University of Texas, Austin, TX (US)

( * ) Notice: Subject to any disclaimer, the term of this patent is extended or adjusted under 35 U.S.C. 154(b) by 0 days.

(21) Appl. No.: 09/275,506

(22) Filed: Mar. 24, 1999

Related U.S. Application Data

(62) Division of application No. 08/437,013, filed on May 8, 1995, now Pat. No. 5,932,220.

(51) Int. Cl.⁷ .............................................. C07H 21/04

(52) U.S. Cl. ...................................... 536/23.7; 530/350

(58) Field of Search .............................. 435/320.1, 325, 435/252.3, 254.11, 257.2; 536/23.7, 24.32, 24.33; 935/3, 9, 11, 12, 22, 66; 530/350

(56) References Cited

U.S. PATENT DOCUMENTS

| | | |
|---|---|---|
| 5,279,938 A | 1/1994 | Rosa |
| 5,283,175 A | 2/1994 | Weaver et al. |

FOREIGN PATENT DOCUMENTS

| | | |
|---|---|---|
| EP | 0 421 725 A1 | 4/1991 |
| WO | 91/19814 | * 12/1991 |
| WO | WO 92/00055 | 1/1992 |
| WO | WO 92/12235 | 7/1992 |

OTHER PUBLICATIONS

Boehringer Mannheim Biochemicals, 1991 Calalog pp. 502 and B–7 to B–8.*
Sloma et al., J. of Bacteriology 173(21): 6889–95, 1991.*
Gassman et al, J. of Bacteriology 173(4): 1452–1459, 1991.*
Jauris–Heipke et al, Med Microbiol. Immunol. 182:37–50, 1993.*
Kennell et al, Prog. Nuc. Acid. Res. Mol. Biol, 11:259–301, 1971.*
Barbour, "Isolation and Cultivation of Lyme Disease Spirochetes," *The Yale Journal of Biology and Medicine*, 57:521–525, 1984.
Barbour and Hayes, "Biology of Borrelia Species," *Microbiological Reviews*, 50(4):381–400, Dec. 1986.
Barbour et al., "A Borrelia–Specific Monoclonal Antibody Binds to a Flagellar Epitope," *Infection and Immunity*, 52(5):549–554, May 1986.
Berland et al., "Molecular Characterization of the Humoral Response to the 41–Kilodalton Flagellar Antigen of *Borrelia burgdorferi*, the Lyme Disease Agent," *Infection and Immunity*, 59(10):3531–3535, Oct. 1991.

Bloemer et al., "Management of Lone Star Ticks (Acari: Ixodidae) in Recreational Areas with Acaricide Applications, Vegetative Management, and Exclusion of White–Tailed Deer," *Journal of Medical Entomology*, 27(4):543–550, Jul. 1990.
"Tickborne Diseases—Georgia, 1989," *MMWR*, 39(23):397–399, Jun. 1990.
"Lyme Disease Surveillance—United States, 1989–1990," *MMWR*, 40(25), Jun. 1991.
Hansen, "Lyme Neuroborreliosis: Improvements of the Laboratory Diagnosis and a Survey of Epidemiological and Clinical Features in Denmark 1985–1990," *Acta Neurol. Scand. Supple. (Denmark)*. 151:1–44, 1994.
Hansen et al., "Measurement of Antibodies to the *Borrelia burgdorferi* Flagellum Improves Serodiagnosis in Lyme Disease," *Journal of Clinical Microbiology*, 26(2):338–346, Feb. 1988.
Kocan et al., "Isolation of *Borrelia–burgdorferi* (Spirochaetales: Spirochaetaceae) from *Ixodes scapularis* and *Dermacentor albipictus* Ticks (Acari: Ixodidae) in Oklahoma," *Journal of Medical Entomology*, 29(4):630–633, Jul. 1992.
Masters, "Erythema Migrans. Rash as Key to Early Diagnosis of Lyme Disease," *Postgraduate Medicine*, 94(1):133–142, Jul. 1993.
Maupin et al., "Landscape Ecology of Lyme Disease in a Residential Area of Westchester County, New York," *American Journal of Epidemiology*, 133(11):1105–1113, 1991.
Mukolwe et al., Attempted Transmission of *Borrelia–burgdorferi* (Spirochaetales: Spirochaetaceae) (JDI Strain) by *Ixodes–scapularis* (Acari: Ixodidae), *Dermacentor–variabilis*, and *Amblyomma–americanum, Journal of Medical Entomology*, 29(4):673–677, Jul. 1992.
Noppa et al., "Expression of the Flagellin Gene in Borrelia is Controlled by an Alternative σ Factor," *Microbiology*, 141:85–93, 1995.
Oliver et al., "Isolation and Transmission of the Lyme Disease Spirochete From the Southeastern United States," *Proc. Natl. Acad. Sci. USA*, 90:7371–7375, Aug. 1993.

(List continued on next page.)

*Primary Examiner*—Patricia A. Duffy
(74) *Attorney, Agent, or Firm*—Fulbright & Jaworski L.L.P.

(57) ABSTRACT

Bites from *Amblyomma americanum*, a hard tick, have been associated with a Lyme disease-like illness in the southeastern and south-central United States. Present in 2% of ticks collected in four states were uncultivable spirochetes. Through use of the polymerase chain reaction, partial sequences of the flagellin and 16s rRNA genes of microorganisms from Texas and New Jersey were obtained. The sequences showed that the spirochete was a Borrelia sp. but distinct from other known members of this genus, including *B. burgdorferi*, the agent of Lyme disease. Species-specific differences in the sequences of the flagellin protein, the flagellin gene and the 16s rRNA gene between the new Borrelia species and previously known species provide compositions and methods for assay for determining the presence of this new spirochete, or for providing evidence of past or present infection by this spirochete in animal reservoirs and humans.

4 Claims, 1 Drawing Sheet

OTHER PUBLICATIONS

Piesmand and Sinsky, "Ability of *Ixodes scapularis, Dermacentor variabilis*, and *Amblyomma americanum* (Acari: Ixodidae) to Acquire, Maintain, and Transmit Lyme Disease Spirochetes (*Borrelia burgdorferi*)," *Journal of Medical Entomology*, 25(5):336–339, Dec. 1988.

Relman, "The Identification of Uncultured Microbial Pathogens," *The Journal of Infectious Diseases*, 168:1–8, Jul. 1993.

Ryder et al., "Inability of *Ixodes cookei* and *Amblyomma americanum* Nymphs (Acari: Ixodidae) To Transmit *Borrelia burgdorferi*," *Journal of Medical Entomology*, 29(3):525–530, May 1992.

Schulze et al., *Amblyomma americanum*: A Potential Vector of Lyme Disease in New Jersey, *Science*, 224:601–603, May 1984.

Sigal and Curran, "Lyme Disease: A Multifocal Worldwide Epidemic," *Annu. Rev. Publ. Health*, 12:85–109, 1991.

Fukunaga et al., "Genetic and Phenotypic Analysis of Borrelia Miyamotoi sp. nov., Isolated from the Ixodid Tick Ixodes Persulcatus, the Vector for Lyme Disease in Japan," *International Journal of Systematic Bacteriology*, 45(4):804–810, Oct. 1995.

Marconi et al., "Phylogenetic Analysis of the Genus Borrelia: a Comparison of North American and European Isolates of Borrelia Burgdorferi," *Journal of Bacteriology*, 174(1):241–244, Jan. 1992.

* cited by examiner

SEQUENCE LISTING

<160> NUMBER OF SEQ ID NOS: 28

<210> SEQ ID NO 1
<211> LENGTH: 641
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
acatattcag atgcagacag aggttctatt caaattgaaa ttgaacaact tacagatgaa      60
attaacagag ttgctgatca ggctcaatac aaccagatgc atatgttatc taacaaatca    120
tctgctcaaa atgtaaaaac tgctgaagag cttggaatgc aacctgcaaa aattaataca    180
ccagcatcac taactggagc acaagcttca tggacattga gagttcaggt aggtgcaaat    240
caggatgaag caattgctgt taatattttc tcaactaatg ttgcaaatct ttttggtgga    300
gaaggtgttc aagcggctcc agctcaagag ggtgcacaac aggagggagt tcaaccagct    360
ccagctcaag gtgggattag ctctccaatt aatgttacaa ctgctattga tgctaatgca    420
tcgcttacaa agattgaaga tgctattaga atggtaactg atcaaagagc aaatcttggt    480
gctttccaaa atagacttga gtctgttaaa gctagcacag attatgctat tgaaaactta    540
aaagcgtctt atgctcaaat taaagatgca ataatgacga tgaaattgt agcatctaca    600 accaacagta ttttgacaca atctgcaatg gctatgattg c                        641

<210> SEQ ID NO 2
<211> LENGTH: 213
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Thr Tyr Ser Asp Ala Asp Arg Gly Ser Ile Gln Ile Glu Ile Glu Gln
  1               5                  10                  15

Leu Thr Asp Glu Ile Asn Arg Val Ala Asp Gln Ala Gln Tyr Asn Gln
                 20                  25                  30

Met His Met Leu Ser Asn Lys Ser Ser Ala Gln Asn Val Lys Thr Ala
             35                  40                  45

Glu Glu Leu Gly Met Gln Pro Ala Lys Ile Asn Thr Pro Ala Ser Leu
     50                  55                  60

Thr Gly Ala Gln Ala Ser Trp Thr Leu Arg Val Gln Val Gly Ala Asn
 65                  70                  75                  80

Gln Asp Glu Ala Ile Ala Val Asn Ile Phe Ser Thr Asn Val Ala Asn
                 85                  90                  95

Leu Phe Gly Gly Glu Gly Val Gln Ala Ala Pro Ala Gln Glu Gly Ala
            100                 105                 110

Gln Gln Glu Gly Val Gln Pro Ala Pro Ala Gln Gly Gly Ile Ser Ser
        115                 120                 125

Pro Ile Asn Val Thr Thr Ala Ile Asp Ala Asn Ala Ser Leu Thr Lys
    130                 135                 140

Ile Glu Asp Ala Ile Arg Met Val Thr Asp Gln Arg Ala Asn Leu Gly
145                 150                 155                 160

Ala Phe Gln Asn Arg Leu Glu Ser Val Lys Ala Ser Thr Asp Tyr Ala

|  |  | 165 |  |  |  | 170 |  |  |  | 175 |  |
|---|---|---|---|---|---|---|---|---|---|---|---|

Ile Glu Asn Leu Lys Ala Ser Tyr Ala Gln Ile Lys Asp Ala Ile Met
                        180                 185                190

Thr Asp Glu Ile Val Ala Ser Thr Thr Asn Ser Ile Leu Thr Gln Ser
        195                 200                205

Ala Met Ala Met Ile
    210

<210> SEQ ID NO 3
<211> LENGTH: 1336
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3

| ctggcagtgc | gtcttaagca | tgcaagtcag | acggaatgta | gtaatacatt | cagtggcgaa | 60 |
|---|---|---|---|---|---|---|
| cgggtgagta | acgcgtggat | aatctgccta | cgagatgggg | ataactatta | gaaataatag | 120 |
| ctaataccga | ataaagtcaa | ttgagttgtt | agttgatgaa | aggaagcctt | taaagcttcg | 180 |
| cttgtagatg | agtctgcgtc | ttattagcta | gttggtaggg | taagagccta | ccaaggctat | 240 |
| gataagtaac | cggcctgaga | gggtgatcgg | tcacactgga | actgagatac | ggtccagact | 300 |
| cctacgggag | gcagcagcta | agaatcttcc | gcaatgggcg | aaagcctgac | ggagcgacac | 360 |
| tgcgtgaacg | aagaaggtcg | aaagattgta | agttcttttt | ataaatgagg | aataagcttt | 420 |
| gtaggaaatg | acaaggtgat | gacgttaatt | tatgaataag | ccccggctaa | ttacgtgcca | 480 |
| gcagccgcgg | taatacgtaa | ggggcgagcg | ttgttcggga | tcattgggcg | taaagggtga | 540 |
| gtaggcggat | atgtaagtct | atgtgtaaaa | taccacggct | caactgtgga | actatgctag | 600 |
| aaactgcatg | actagagtct | gatagggaa | gttagaattc | ctggtgtaag | ggtggaatct | 660 |
| gttgatatca | ggaagaatac | cagaggcgaa | agcgaacctc | taggtcaaga | ctgacgctga | 720 |
| gtcacgaaag | cgtagggagc | aaacaggatt | agataccctg | gtagtctacg | ctgtaaacga | 780 |
| tgcacacttg | gtgttaatcg | aaaggttagt | accgaagcta | acgtgttaag | tgtgccgcct | 840 |
| ggggagtatg | ctcgcaagag | tgaaactcaa | aggaattgac | gggggcccgc | acaagcggtg | 900 |
| gagcatgtgg | tttaattcga | tgatacgcga | ggaaccttac | cagggcttga | catatacagg | 960 |
| atatagttag | agataactac | tctccgtttg | gggtctgtat | acaggtgctg | catggttgtc | 1020 |
| gtcagctcgt | gctgtgaggt | gttgggttaa | gtcccgcaac | gagcgcaacc | cttgttgtct | 1080 |
| gttaccagca | tgtaaagatg | gggactcaga | cgagactgcc | ggtgataagc | cggaggaagg | 1140 |
| tgaggatgac | gtcaaatcat | catggccctt | atgtcctggg | ctacacacgt | gctacaatgg | 1200 |
| cctgtacaaa | gcgatgcgaa | acagtgatgt | gaagcaaaac | gcataaagca | ggtctcagtc | 1260 |
| cagattgaag | tctgaaactc | gacttcatga | agttggaatc | gctagtaatc | gtatatcaga | 1320 |
| atgatacggt | gaatac |  |  |  |  | 1336 |

<210> SEQ ID NO 4
<211> LENGTH: 330
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4

```
aactgctgaa gagcttggaa tgcaacctgc aaaaattaat acaccagcat cactaactgg      60
agcacaagct tcatggacat tgagagttca ggtaggtgca aatcaggatg aagcaattgc     120
tgttaatatt ttctcaacta atgttgcaaa tctttttggt ggagaaggtg ttcaagcggc     180
tccagctcaa gagggtgcac aacaggaggg agttcaacca gctccagctc aaggtgggat     240
tagctctcca attaatgtta caactgctat tgatgctaat gcatcgctta caaagattga     300
agatgctatt agaatggtaa ctgatcaaag                                       330
```

```
<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Gly Val Gln Ala
  1
```

```
<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6 tctgctcaa                                                               9
```

```
<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ggtgttcaag cg                                                          12
```

```
<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gttcaaccag ct                                                          12
```

```
<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
aacagctgaa gagcttggaa tg                                               22
```

```
<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
cgataatctt actattcact agtttc                                          26

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
acatattcag atgcagacag aggt                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tgttagacgt taccgttact aacg                                            24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ctggcagtgc gtcttaagca                                                 20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
catatagtct tactatgcca cttag                                           25

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Leu Arg Val Gln Val Gly Ala Asn Gln Asp Glu Ala Ile Ala Val Asn
 1               5                  10                  15

Ile Phe Ser Thr Asn Val Ala Asn Leu Phe Gly Gly Glu Gly Val
```

20                  25                  30

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Gln Ala Ala Pro Ala Gln Glu Gly Ala Gln Gln Glu Gly Val Gln Pro
 1               5                  10                  15

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Ala Pro Ala Gln Gly Gly Ile Ser Ser Pro Ile Asn Val Thr Thr Ala
 1               5                  10                  15

Ile Asp Ala Asn
            20

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Ala Ala Pro Ala Pro Ala Ala
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Ala Thr Pro Ala Pro Val Ala
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Ala Ala Pro Ala Pro Ala Ser
 1               5

<210> SEQ ID NO 21
<211> LENGTH: 4
<212> TYPE: PRT

```
<213> ORGANISM: Artificial Sequence
<220> FEATURE:
<223> OTHER INFORMATION: Description of Artificial Sequence: Synthetic
      Peptide

<400> SEQUENCE: 21

Ala Gln Ala Ala
  1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Pro Thr Pro Ala Thr
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Pro Ala Pro Val Thr
  1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ala Gln Thr Ala
  1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Pro Ala Pro Ala Thr
  1               5

<210> SEQ ID NO 26
<211> LENGTH: 709
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
aacaacaacc tcgggatcga gggaaggatt tcagaattca catattcaga tgcagacaga      60
```

-continued

```
ggttctattc aaattgaaat tgaacaactt acagatgaaa ttaacagagt tgctgatcag      120
gctcaataca accagatgca tatgttatct aacaaatcat ctgctcaaaa tgtaaaaact      180
gctgaagagc ttggaatgca acctgcaaaa attaatacac cagcatcact aactggagca      240
caagcttcat ggacattgag agttcaggta ggtgcaaatc aggatgaagc aattgctgtt      300
aatattttct caactaatgt tgcaaatctt tttggtggag aaggtgttca agcggctcca      360
gctcaagagg gtgcacaaca ggaaggagtt caaccagctc cagctcaagg tgggattagc      420
tctccaatta atgttacaac tgctattgat gctaatgcat cgcttacaaa gattgaagat      480
gctattagaa tggtaactga tcaaagagca atcttggtg ctttccaaaa tagacttgag       540
tctgttaaag ctagcacaga ttatgctatt gaaaacttaa aagcgtctta tcgtcaaatt      600
aaagatgcaa taatgacaga tgaaattgta gcatctacaa ccaacagtat tttgacacaa      660
tctgcaatgg ctatgattgc agtctagagt cgacctgcag gcaagcttg                 709

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Ile Ser Glu Phe
  1

<210> SEQ ID NO 28
<211> LENGTH: 641
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
acatattcag atgcagacag aggttctatt caaattgaaa ttgaacaact tacagatgaa       60
attaacagag ttgctgatca ggctcaatac aaccagatgc atatgttatc taacaaatca      120
tctgctcaaa atgtaaaaac tgctgaagag cttggaatgc aacctgcaaa aattaataca      180
ccagcatcac taactggagc acaagcttca tggacattga gagttcaggt aggtgcaaat      240
caggatgaag caattgctgt taatattttc tcaactaatg ttgcaaatct ttttggtgga      300
gaaggtgttc aagcggctcc agctcaagag ggtgcacaac aggaaggagt tcaaccagct      360
ccagctcaag gtgggattag ctctccaatt aatgttacaa ctgctattga tgctaatgca      420
tcgcttacaa agattgaaga tgctattaga atggtaactg atcaaagagc aatcttggt       480 gctttccaaa atagacttga gtctgttaaa gctagcacag attatgctat tgaaaactta      540
aaagcgtctt atgctcaaat taaagatgca ataatgacag atgaaattgt agcatctaca      600
accaacagta ttttgacaca atctgcaatg gctatgatgg c                         641
```

DIAGNOSTIC TEST FOR BORRELIA INFECTION

This is a divisional of application Ser. No. 08/437,013, filed May 8, 1995 now U.S. Pat. No. 5,932,220.

The government owns rights in the present invention pursuant to grant number AI24424 from the National Institutes of Health.

FIELD OF THE INVENTION

The present invention relates generally to the fields of infection and disease. More particularly, it concerns the identification of a new spirochete carried by the hard tick, *Amblyomma americanum*, found by the present inventor to be associated with a Lyme disease-like illness in the southeastern and south-central United States. Most particularly, the invention provides compositions, methods, and kits for the identification of the new spirochete for diagnostic purposes.

DESCRIPTION OF THE RELATED ART

A paradox about Lyme disease is the report of this tick-borne infection from areas in which transmission of the etiologic agent, *B. burgdorferi*, has not been documented (Sigal et al., 1991; Barbour et al., 1993). This phenomenon has been reported from Georgia and Missouri, but may be common in other parts of the southeastern and south-central United States (Centers for Disease Control and Prevention, 1989; 1991). The Lyme disease-like illness is a localized, expanding circular skin rash, sometimes succeeded by persistent, debilitating systemic symptoms (Masters, 1993; Donnell, 1992). Many of the patients with this illness have had negative serologic assays for antibodies to *B. burgdorferi*, a finding that has fueled a controversy about so-called "seronegative Lyme disease" (Sigal et al., 1991; Barbour et al., 1993). Although *Ixodes scapularis* ticks, the usual vector of the Lyme disease agent, has been identified in some of these geographic areas, the more commonly reported exposure for these patients has been to another hard tick, *A. americanum*, known as the "Lone Star tick" (Centers for Disease Control and Prevention 1989; 1991; Masters, 1993; Donnell, 1992). One conclusion from these observations is that the disease is caused by something other than *B. burgdorferi* and that the vector of the putative agent is *A. americanum* (Maupin et al., 1992).

The incompetence of *A. americanum* as a vector of *B. burgdorferi* has been documented (Piesman et al., 1988; Mather et al., 1990; Mukolwe et al., 1992; Ryder et al., 1992). Nevertheless, there have been descriptions in these ticks of spirochetes that cross-react with antibodies to the Lyme disease agents (Maupin et al., 1992; Schulze et al., 1984). Until the discovery of *B. burgdorferi* and related Borrelia species in Ixodes spp. ticks a decade ago, Borrelia spp. had almost exclusively been found in soft or argasid ticks (Barbour et al., 1986).

Reports from several locations in the southeastern and south-central regions of the United States indicate that this Lyme disease-like illness, which is apparently ameliorated by antibiotics, is associated with bites by the Lone Star tick (Centers for Disease Control and Prevention, 1989; 1991; Masters, 1993; Donnell, 1992). *A. americanum* is a common person-biting tick in these areas (Cooney et al., 1974; Koch et al., 1980; Hair et al., 1986; Bloemer et al., 1990). Its usual hosts are white-tailed deer, medium-sized mammals, and ground-feeding birds; rodents are only rarely infested by *A. americanum*. The tick's distribution extends from west-central Texas to Florida and north to Rhode Island (Cooney et al., 1974; Koch et al., 1980; Hair et al., 1986; Bloemer et al., 1990).

Numerous references in the literature relate to aspects of diagnosing and treating Lyme disease. For example: i) U.S. Pat. No. 5,279,938 relates to a nucleotide sequence of a recombinant clone containing a specific segment of *Borrelia burgdorferi* (Bb) DNA, the causative agent of Lyme disease; ii) an abstract by Barthhold (WPI Acc. No.: 92-041321/05) relates to OSPA polypeptides immuno-reactive with antibodies generated by the spirochete *Borrelia burgdorferi*; iii) The Weisburg world patent publication relates to nucleic acid fragments that are used to detect the etiological agent of Lyme disease, Borrelia; iv) The Oliver et al. (1993) abstract relates to a study of the isolation and transmission of the Lyme disease spirochete; v) The Berland et al. (1991) abstract relates to the characterization of a 41 kDa flagellin antigen of *B. burgdorferi*; vi) The Mukolwe et al. (1992) article relates to attempts to transmit the *B. burgdorferi* (Bb) spirochete to three different ticks, one of these being the *Amblyomma americanum* tick. The test results report transfer of the Bb spirochete only to Ixodes scapularis ticks.

Although there is much known about Lyme disease, there are currently no means of identification of the new spirochete associated with the aforedescribed Lyme disease-like pathology and further, no means of diagnosis of infection, compositions for clinical tests, or laboratory assays for diagnosing a patient exhibiting Lyme disease-like symptoms but testing negative for Lyme disease.

SUMMARY OF THE INVENTION

The present invention provides compositions, methods, and kits for the detection of a new spirochete that is associated with a Lyme disease-like illness. The compositions are based on a *Borrelia lonestari* sp. nov.-specific allotype or combination of allotypes of the flagellin protein, or a *Borrelia lonestari* sp. nov.-specific allele or combination of alleles of the flagellin or 16s rRNA genes of the new spirochete. The allotypes and alleles provided by the present invention have been determined by nucleic acid sequencing of portions of the flagellin and rRNA genes from this new spirochete. Detection of a species-specific amino acid or nucleotide as defined herein, or a species-specific combination of amino acids or nucleotides as defined herein, in a subject sample is indicative of infection with *Borrelia lonestari* sp. nov.

"Species-specific allotype" or "species-specific amino acid" or "species-specific epitope" means an amino acid of *B. lonestari* sp. nov. that is different at a particular position of the flagellin protein amino acid sequence than the amino acid at that position of the flagellin protein of other Borrelia species, especially those species needing to be distinguished from *B. lonestari* sp. nov. Table 1 provides a listing of species-specific amino acids of this new spirochete in the context of the amino acid sequence of SEQ ID NO: 2.

"Species-specific combination of allotypes" or "species-specific combination of amino acids" or "species-specific combination of epitopes" is a combination of amino acids of the flagellin protein of *B. lonestari* sp. nov. from Table 1 that is not represented in any of the flagellin proteins of other Borrelia species, especially those species needing to be distinguished from *B. lonestari* sp. nov. Table 1 also provides a listing of amino acids that may be combined with each other to form a combination that is unique to *B. lonestari* sp. nov. in the context of the amino acid sequence of SEQ ID NO: 2.

"Species-specific allele" or "species-specific nucleotide" means a nucleotide of B. lonestari sp. nov. that is different at a particular position of the flagellin gene sequence or 16s rRNA gene sequence from the nucleotide at that position of other flagellin gene sequences or 16s rRNA gene sequences of Borrelia species, especially the Borrelia species that need to be particularly distinguished, like B. burgdorferi. Tables 2 and 3 provide a listing of species-specific nucleotides of this new spirochete in the context of SEQ ID NO: 1 and 3.

"Species-specific combination of alleles" or "species-specific combination of nucleotides" is a combination of nucleotides of the flagellin gene or 16s rRNA gene of B. lonestari sp. nov. from Table 2 or 3 that is not represented in any of the flagellin gene sequences or 16s rRNA gene sequences of other Borrelia species. Tables 2 and 3 provide a listing of nucleotides that may be combined with each other to form a combination that is unique to B. lonestari sp. nov. in the context of SEQ ID NO: 1 and 3.

Species-specific flagellin amino acids of B. lonestari sp. nov. are listed in Table 1 as the underlined residues in the column Bl and include Val 24, Thr 65, Ala 67, Phe 90, Ser 91, Thr 92, Gly 99, Val 103, Pro 119, Ile 126, Ser 127, Ile 136, Ala 140, Thr 144, Asp 174, and Ile 191, of SEQ ID NO:2.

Species-specific flagellin nucleotides of B. lonestari sp. nov. are listed in Table 2 as the underlined nucleotides in the column Bl and include G 70, G 96, T 141, A 193, G 199, G 228, A 231, T 269, C 270, T 271, A 273, A 300, T 308, G 315, A 376, G 380, A 406, G 418, G 423, G 505, A 510, G 546, T 572, and C 603 of SEQ ID NO:1.

Exemplary species-specific combinations of amino acids where the amino acid itself is not species-specific are found by comparing the amino acids of Table 1 and finding a combination of Bl amino acids that is not represented in any of the other species listed in the context of the flagellin amino acid sequences of these organisms. Examples include: amino acid #s 41 and 46, 46 and 108, 117 and 153, 130 and 153, 46 and 147, 152 and 169, 152 and 171, and 46 and 196 of SEQ ID NO:2, for example.

Of course, Tables 1 and 2 clearly demonstrate the differences in amino acids and nucleotides of the flagellin proteins and genes of B. lonestari sp. nov. and B. burgdorferi, the causative agent of Lyme disease in North America (Barbour and Fish, 1993) and the most relevant organism to distinguish B. lonestari sp. nov. from in a diagnostic test.

Exemplary species-specific combinations of nucleotides where the nucleotide itself is not species-specific are found by comparing the nucleotides of Table 2 and finding a combination of Bl nucleotides that is not represented in any of the other species listed in the context of the sequence of SEQ ID NO: 1. Examples include: nucleotide NT #30 and 225, 42 and 225, 177 and 297, 303 and 312, 350 and 355, 375 and 419, 432 and 435, 458 and 475, and 501 and 516 of SEQ ID NO:1, for example. With these examples, one skilled in the art would, upon further examination of Table 2, find further species-specific combinations of nucleotides in the context of SEQ ID NO: 1 for identification of B. lonestari sp. nov.

An embodiment of the present invention is a purified nucleic acid molecule comprising a nucleotide sequence of about 12 to about 709 nucleotides that encodes a B. lonestari sp. nov. flagellin peptide having at least one B. lonestari sp. nov.-specific amino acid or species-specific combination of amino acids from Table 1, or a complement thereof. In a preferred embodiment, the nucleotide sequence has the sequence of SEQ ID NO:1, 4 or 26. An even more preferred embodiment is a purified nucleic acid molecule having a nucleotide sequence encoding a protein having an amino acid sequence of SEQ ID NO: 2, a partial sequence of the B. lonestari sp. nov. flagellin protein.

Further embodiments include a recombinant molecule comprising the nucleic acid molecule described above, a host cell comprising the recombinant molecule and the recombinant molecule is preferably an expression vector. The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

The at least one B. lonestari sp. nov. specific amino acid may be at position 24, 65, 67, 90, 91, 92, 99, 103, 119, 126, 127, 136, 140, 174, or 191 of SEQ ID NO:2 as shown in Table 1. The at least one B. lonestari sp. nov.-specific combination of amino acids is also obtained from Table 1 as described above.

TABLE 1

Comparison of Amino Acids at Designated Positions of the Flagellin Protein of Various Borrelia Species

| Aa#[1] | Bl[2] | Bb | Ba | Bh | Bc | Bz |
|---|---|---|---|---|---|---|
| 24 | V[3,6] | I | I | I | I | I |
| 41 | S | A | A | A | S | A |
| 42 | A | S | A | A | A | S |
| 46 | K | R | R | K | R | K |
| 65 | T | S | S | A | S | S |
| 67 | A | S | S | S | S | S |
| 90[4] | F | Y | Y | Y | Y | Y |
| 91 | S | A | A | A | A | A |
| 92 | T | A | A | S | A | A |
| 99 | G | S | A | A | S | A |
| 103 | V | A | A | A | A | A |
| Δ104 | —[5] | Q | — | — | Q | Q |
| Δ105 | — | AA | — | — | — | AA |
| 108 | A | V | A | V | A | V |
| 112 | A | V | A | G | A | A |
| 117 | V | A | V | V | A | A |
| 119 | P | Q | A | A | A | Q |
| Δ120 | — | 5 amino acids | 6 amino acids | 6 amino acids | 6 amino acids | 5 amino acids |
| 122 | A | S | A | A | A | T |
| 126 | I | V | V | V | V | V |
| 127 | S | N | N | N | N | N |
| 130 | I | V | I | I | V | V |
| 135 | A | T | A | A | A | T |
| 136 | I | V | V | V | V | V |
| 140 | A | T | M | M | M | T |
| 144 | T | A | A | A | T | A |
| 147 | D | N | D | G | D | N |
| 152 | V | I | V | V | I | I |
| 153 | T | S | S | S | T | S |
| 169 | V | I | I | I | V | I |
| 171 | A | N | D | D | A | N |
| 174 | D | E | E | E | E | E |
| 191 | I | T | T | T | T | T |

TABLE 1-continued

Comparison of Amino Acids at Designated Positions of the Flagellin Protein of Various Borrelia Species

| Aa#[1] | Bl[2] | Bb | Ba | Bh | Bc | Bz |
|---|---|---|---|---|---|---|
| 196 | I | V | I | V | I | V |
| 199 | S | A | S | S | S | A |

[1]Aa#: amino acid number from SEQ ID NO:2.
[2]Abbreviations: Bl, *Borrelia lonestari* sp. nov.; Bb, *B. burgdorferi*; Ba, *B. anserina*; Bh, *B. hermsii*; Bc, *B. crocidurae*; Bz, *B afzelii*.
[3]Underline: Amino acid positions that are species-specific to Bl.
[4]Italics indicate positions or a range of amino acid positions where a peptide would be species-specific for Bl.
[5]—, deletion.
[6]Amino acids have three and one letter designations as follows, either designation may be used herein: Alanine = Ala (A); Arginine = Arg (R); Aspartate = Asp (D); Asparagine = Asn (N); Cysteine = Cys (C); Glutamate = Glu (E); Glutamine = Gln (Q); Glycine = Gly (G); Histidine = His (H); Isoleucine = Ile (I); Leucine = Leu (L); Lysine = Lys (K); Methionine = Met (M); Phenylalanine = Phe (F); Proline = Pro (P); Serine = Ser (S); Threonine = Thr (T); Tryptophan = Trp (W); Tyrosine = Tyr (Y); Valine = Val (V).

The at least one *B. lonestari* sp. nov.-specific amino acid or combination of amino acids can be considered an allotype of this species. Preferably, the length of the oligonucleotide is from about 12 to about 641 nucleotides; or in other embodiments, from about 12 to about 330 nucleotides; or 12 to about 300; or 12 to about 150; or 12 to about 99; and in still other embodiments, from about 15 to about 30 nucleotides. In other embodiments, the nucleotide sequence encodes amino acid(s) at and flanking position 24, 65, 67, 90, 91, 92, 99, 103, 119, 126, 127, 136, 140, 174, or 191 of SEQ ID NO:2. Preferably, the sequence encodes amino acids at and flanking positions 90–92, 103–108, 119–127, 136–144, or 171–174 of SEQ ID NO:2. In another embodiment, the sequence encodes a species-specific combination of amino acids of Table 1 having flanking amino acids from SEQ ID NO:2. The oligonucleotide may be defined further as including a detectable label. Some oligonucleotides may be defined further as comprising the sequence GGTGTTCAAGCG, SEQ ID NO:7 or GTTCAACCAGCT, SEQ ID NO:8. These sequences are unique to *B. lonestari* sp. nov. due to the presence of a number of nucleotides at particular positions around 310 and 358 of the flagellin gene of other Borrelia species. These species-specific oligonucleotides are useful as hybridization probes for the detection of *B. lonestari* sp. nov. in a diagnostic assay.

A further embodiment of the invention is a purified nucleic acid molecule comprising a nucleotide sequence represented in SEQ ID NO:1 or 3 having at least one *B. lonestari* sp. nov.-specific nucleotide or species-specific combination of nucleotides from Table 2 or 3, or a complement thereof. Another embodiment is a purified flagellin gene of *B. lonestari* sp. nov. A further embodiment of the present invention is a nucleic acid segment that comprises at least a 10–14 nucleotide long stretch that corresponds to, or is complementary to, the nucleic acid sequence of SEQ ID NO:1 and includes an allele as described in Table 2. In a more preferred embodiment, the nucleic acid is further defined as comprising at least about a 20 nucleotide long stretch, about 30 nucleotide long stretch, about 50 nucleotide long stretch, about 100 nucleotide long stretch, about 200 nucleotide long stretch, about 400 nucleotide long stretch, about 600 nucleotide long stretch, or a full length sequence that corresponds to, or is complementary to, the nucleic acid sequence of SEQ ID NO:1 and includes an allele as described in Table 2.

TABLE 2

Comparison of Nucleotides at Designated Positions of the Flagellin Gene as Listed in SEQ ID NO:1 for Various Borrelia Species

| Nt#[1] | Bl[2] | Bb | Ba | Bh | Bc | Bz |
|---|---|---|---|---|---|---|
| 30 | T | A | T | T | T | A |
| 42 | T | A | T | T | T | A |
| 45 | A | G | G | G | A | G |
| 57 | T | C | T | T | T | C |
| 62 | T | T | T | C | C | T |
| 66 | C | T | C | C | T | T |
| 70[3] | G[4] | A | A | A | A | A |
| 81 | G | A | A | G | A | G |
| 90 | C | T | T | C | T | T |
| 96 | G | A | A | A | T | A |
| 102 | T | C | T | T | T | C |
| 108 | A | A | G | G | A | G |
| 117 | A | A | G | G | A | A |
| 120 | A | T | A | A | A | T |
| 121 | T | G | G | G | T | G |
| 124 | G | T | G | G | G | T |
| 137 | A | G | G | A | G | A |
| 141 | T | A | A | A | A | A |
| 177 | T | C | T | C | T | C |
| 192 | A | T | A | A | A | T |
| 193 | A | T | T | G | T | T |
| 199 | G | T | T | T | T | T |
| 201 | A | T | A | A | A | T |
| 210 | A | T | A | A | A | T |
| 219 | G | A | A | G | A | A |
| 225 | T | T | A | A | A | T |
| 228 | G | T | T | T | T | T |
| 231 | A | T | G | G | T | G |
| 234 | T | A | T | C | T | A |
| 261 | T | A | T | T | T | A |
| 269 | T | A | A | A | A | A |
| 270 | C | T | T | T | T | T |
| 271 | T | G | G | G | G | G |
| 273 | A | G | G | T | G | G |
| 295 | G | T | G | G | T | G |
| 297 | T | T | A | A | A | T |
| 300 | A | T | T | T | T | T |
| 303 | A | G | A | A | G | G |
| 306 | T | A | T | C | T | A |
| 308 | T | C | C | C | C | C |
| Δ310 | — | CAA | — | — | CAA | CAA |
| Δ311 | — | ACTGCT | — | — | — | GCTGCT |
| 312 | A | G | G | G | A | G |
| 315 | G | T | T | T | T | T |
| 318 | T | A | T | T | T | A |
| 321 | A | G | A | A | A | T |
| 323 | C | T | C | T | C | T |
| 333 | T | T | A | A | T | T |
| 336 | A | T | A | A | A | T |
| 339 | A | A | A | G | G | A |
| 342 | G | G | A | A | A | A |
| 350 | T | C | T | G | C | C |
| 355 | C | C | G | G | G | C |
| 356 | C | A | C | C | C | A |
| Δ358 | — | N$_{15}$ | N$_{18}$[5] | N$_{18}$ | N$_{18}$ | N$_{15}$ |
| 360 | T | A | T | T | T | A |
| 363 | A | T | A | A | A | T |
| 375 | G | A | G | A | A | A |
| 376 | A | G | G | G | G | G |
| 380 | G | A | A | A | A | A |
| 387 | A | T | A | A | A | T |
| 388 | A | G | A | A | G | G |
| 402 | T | T | T | C | T | T |
| 403 | G | A | G | G | G | A |
| 405 | T | A | T | T | T | A |
| 406 | A | G | G | G | G | G |
| 418 | G | A | A | A | A | A |
| 419 | C | C | T | T | T | C |
| 420 | A | A | G | G | A | A |
| 423 | G | A | A | A | A | A |
| 427 | A | G | G | G | A | G |
| 429 | A | T | A | A | A | T |
| 432 | G | A | G | G | A | A |

TABLE 2-continued

Comparison of Nucleotides at Designated Positions of
the Flagellin Gene as Listed in SEQ ID NO:1
for Various Borrelia Species

| Nt#[1] | Bl[2] | Bb | Ba | Bh | Bc | Bz |
|---|---|---|---|---|---|---|
| 435 | T | T | A | A | G | A |
| 439 | G | A | G | G | A | A |
| 454 | G | A | G | G | C | A |
| 458 | C | G | G | G | C | G |
| 475 | C | T | C | C | T | T |
| 477 | T | A | T | T | C | A |
| 492 | T | T | T | C | A | T |
| 501 | G | A | A | G | G | A |
| 505 | G | A | A | A | A | A |
| 510 | A | G | G | G | G | G |
| 512 | C | A | A | A | C | A |
| 516 | C | T | C | T | A | C |
| 519 | A | T | A | A | G | T |
| 522 | T | G | A | A | T | G |
| 537 | C | T | C | C | T | T |
| 538 | T | C | T | T | T | C |
| 546 | G | A | A | A | T | A |
| 561 | T | A | T | T | A | A |
| 570 | A | T | A | A | C | T |
| 572 | T | C | C | C | A | C |
| 585 | A | G | A | A | A | G |
| 586 | A | G | A | G | T | G |
| 595 | T | G | T | T | T | G |
| 597 | T | A | T | A | T | T |
| 603 | C | T | T | T | A | T |
| 606 | C | T | C | C | C | T |
| 615 | G | A | A | G | G | A |
| 633 | T | A | T | T | T | A |

Nt#[1]: nucleotide number from SEQ ID NO:1
[2]Abbreviations: Bl, *Borrelia lonestari* sp. nov.; Bb, *B. burgdorferi*; Ba, *B. anserina*; Bh, *B. hermsii*; Bc, *B. crocidurae*; Bz, *B. afzelii*.
[3]Italicized nucleotide positions indicate a location or range of locations where an oligonucleotide would be species-specific for Bl.
[4]Nucleotide positions at which the nucleotide for Bl is unique and, therefore, species-specific, are underlined.
[5]N$_{15,18}$ = a 15 or 18 nucleotide insert is present in these species compared to *B. lonestari* sp. nov., therefore, the sequence of nucleotides at this region of *B. lonestari* is species-specific.

TABLE 3

*B. lonestari* sp. nov.-Specific 16s rRNA Gene Nucleotides[1]

| Nucleotide #'s of SEQ ID NO:3 that provide novel combinations | Nucleotide(s) in 16s rRNA gene that provide novel combinations |
|---|---|
| 135, 146, 217 | A, T, A |
| 146, 217, 224 | T, A, G |
| 217, 224, 267 | A, G, T |
| 224, 267, 435 | G, T, G |
| 267, 435 | T, G |
| 435, 437, 522 | G, T, C |
| 437, 522 | T, C |
| 437, 522, 554 | T, C, T |
| 522, 554 | C, T |
| 522, 554, 564 | C, T, T |
| 554, 564 | T, T |
| 554, 564, 963 | T, T, A |

[1]From Table 6 and comparison of SEQ ID NO:3 with sequences presented in sequence data base such as GenBank having accession numbers corresponding to those of footnote of Table 5.

The present invention also encompasses DNA segments which are complementary, or essentially complementary, to the sequence set forth in SEQ ID NO:1, 3, 4 or 26 or other of the segments described herein. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleqtide comparison set forth above, or as defined as being capable of hybridizing to the nucleic acid segment of SEQ ID NO:1, 3, 4 or 26 under relatively stringent conditions such as those described herein. The *B. lonestari* sp. nov. nucleotides set forth in Tables 2 and 3, however, are considered relatively invariant since they are species-specific or a combination of the nucleotides is species-specific.

A purified nucleic acid molecule comprising a nucleotide sequence encoding a *B. lonestari* sp. nov. 16s ribosomal RNA is a further embodiment of the present invention. Preferably, the nucleotide sequence has a sequence comprising SEQ ID NO:3. The nucleic acid may be defined further as a recombinant molecule.

A preferred embodiment of the present invention is a purified flagellin protein of *B. lonestari* sp. nov. The protein may be defined further as an amino acid sequence comprising SEQ ID NO:2. The term "the amino acid sequence of SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein as having the amino acids of SEQ ID NO:2 listed in Table 1, these amino acids being relatively invariant in their function as species-specific epitopes or combination of epitopes of *B. lonestari* sp. nov. The flagellin protein or portions thereof having species-specific epitopes or a combination of epitopes is useful in an immunoassay for the detection of *B. lonestari* sp. nov.

A purified peptide having an amino acid sequence comprising about 6 to about 213 amino acids of SEQ ID NO:2 that includes at least one *B. lonestari* sp. nov.-specific amino acid or species-specific combination of amino acids from Table 1 is a further embodiment of the present invention. Preferably, the peptide has from about 6 to about 212 amino acids; more preferably, from about 6 to about 150 amino acids; and in other embodiments, from about 6 to about 50 amino acids. The above-described peptide preferably includes *B. lonestari* sp. nov. specific amino acid(s) at and flanking position 24, 65, 67, 90, 91, 92, 99, 103, 119, 126, 127, 136, 140, 174, or 191 of SEQ ID NO:2. Preferably, the peptide includes amino acid(s) at and flanking positions 90–92, 103–108, 119–127, 136–144, or 171–174 of SEQ ID NO:2. In another embodiment, the peptide includes a species-specific combination of amino acids of Table 1 having flanking amino acids from SEQ ID NO:2. In some embodiments, the peptide may include a detectable label. Preferred peptides comprise the sequence Gly Val Gln Ala, SEQ ID NO:5 or the sequence Val Gln Pro. These sequences are unique to *B. lonestari* sp. nov. due to the presence of a number of nucleotides at particular positions of the flagellin gene of other Borrelia species. These species-specific peptides are useful as epitopes for the detection of antibodies having specificity for a species-specific flagellin protein, for the detection of T cells or B cells having similar specificity, or as antigens in an immunoassay for the detection of *B. lonestari* sp. nov. or for the generation of antibodies to be used in an immunoassay.

A fusion protein or peptide comprising a segment of SEQ ID NO:2 having at least one *B. lonestari* sp. nov.-specific amino acid or species-specific combination of amino acids of Table 1 is also an aspect of the present invention. The fusion protein preferably comprises SEQ ID NO:26, however, one skilled in the art, in light of the present disclosure, would be able to construct a number of different fusion proteins from a variety of vectors and the *B. lonestari* sp. nov. DNA sequences provided herein. It will also be understood that amino acid and nucleic acid sequences may include additional residues, such as additional N- or C-terminal amino acids, and yet still be essentially as set forth in one of the sequences disclosed herein, so long as the sequence meets the criteria set forth above. Segments of the flagellin gene may be cloned next to N- and/or C-terminal sequences of genes for other proteins, such as, β-galactosidase or maltose binding protein. A signal peptide that may allow better expression may be optionally included in the fusion protein. It is not necessary that the flagellin protein be transported, however, the signal peptide may help to prevent protease digestion.

A preferred embodiment of the present invention is a method of detecting *B. lonestari* sp. nov. in a subject. The method comprises the step of contacting a nucleic acid sample from the subject with an oligonucleotide comprising a nucleotide sequence of about 12 to about 30 nucleotides from SEQ ID NO:1 that includes at least one *B. lonestari* sp. nov.-specific nucleotide or species-specific combination of nucleotides from Table 2 or 3, or a complement thereof, under conditions allowing hybridization to form a duplex, wherein duplex formation indicates the presence of *B. lonestari* sp. nov. Preferably, the nucleotide sequence comprises the sequence GGTGTTCAAGCG, SEQ ID NO:7 or GTTCAACCAGCT, SEQ ID NO:8. The oligonucleotide may comprise a detectable label and the complex may then be detected by reference to the label.

A further method of detecting *B. lonestari* sp. nov. in a subject comprises the steps of amplifying a segment of DNA from the subject using a set of PCR™ primers, wherein the segment of DNA includes at least one *B. lonestari* sp. nov.-specific nucleotide or species-specific combination of nucleotides from Table 2 or 3, and determining the nucleotide sequence of the segment. When the nucleotide sequence of the segment is found in SEQ ID NO:1 or 3, or a complement thereof, then *B. lonestari* sp. nov. is detected. The PCR™ primers may be designed to be complementary to a region of SEQ ID NO: 1 or 3 or to sequences 5' and 3' to any segment to be amplified, and the primers may be complementary to a sequence outside of the herein defined sequences, i.e., in flanking vector or naturally occurring sequences, for example. It is contemplated that regions of as few as 20 or 50 bases may be amplified, or as long as 500 or 1000 bases. One of skill in this art would also understand, in light of the present disclosure, that other means of amplification of DNA or RNA segments would also be applicable to the techniques defined herein.

The present invention also provides a method of detecting *B. lonestari* sp. nov. in a subject comprising the step of analyzing a DNA sample from the subject for a restriction fragment length polymorphism that is unique to *B. lonestari* sp. nov. A preferred restriction fragment length polymorphism is from an AluI restriction enzyme digest.

Another embodiment of the present invention is a method of detecting a previously elicited immune response to *B. lonestari* sp. nov. in a subject. This method may be a cell mediated immunity test. The method comprises the step of contacting a sample from the subject with an epitope having at least a partial amino acid sequence of SEQ ID NO:2 that includes at least one *B. lonestari* sp. nov.-specific amino acid or species-specific combination of amino acids from Table 1, is also an embodiment of the present invention. Contacting of the sample would be under conditions allowing epitope-antibody or epitope-T cell binding to occur to form a complex, and complex formation indicates the presence of a previously elicited immune response to *B. lonestari* sp. nov. Preferably, the epitope is bound to a detectable label, and a preferred epitope is a flagellin fusion protein. The present inventors also envision the detection of B cells secreting antibody having epitope specificity as defined herein.

A method of detecting *B. lonestari* sp. nov. in a subject comprising the step of contacting a sample from the subject with an antibody having binding specificity for an epitope having an amino acid sequence from SEQ ID NO:2 that includes at least one *B. lonestari* sp. nov.-specific amino acid or species-specific combination of amino acids from Table 1 is also an embodiment of the present invention. The contacting is under conditions allowing epitope-antibody binding to occur to form a complex and complex formation indicates the presence of *B. lonestari* sp. nov. Preferably, the epitope has a number of amino acids less than that of SEQ ID NO:2. In these immunoassay procedures, a further step of contacting the complex with a detectably labeled antibody having binding specificity for the complex may be included.

Most preferably, the subject of these detection methods is a human suspected of being infected with *B. lonestari* sp. nov., although suspected animal reservoirs are also preferred. Any animal that may have been bitten by a tick and that may carry this new spirochete may be tested, including domestic animals such as dogs, cats, cattle, or turkeys, for example.

A test kit for the detection of *B. lonestari* sp. nov. in a biological sample is also an aspect of the present invention. A kit may comprise in packaged combination; a carrier means adapted to receive a plurality of container means in close confinement therewith; a first container means including an oligonucleotide comprising a nucleotide sequence that includes at least one *B. lonestari* sp. nov.-specific nucleotide or species-specific combination of nucleotides from Table 2 or 3, or a complement thereof; and at least one microtiter plate. The oligonucleotide may encode all of SEQ ID NO:2 or a portion thereof.

Alternatively, a kit may have a first container means including a first antibody having binding specificity for an epitope, the epitope having a partial or complete amino acid sequence of SEQ ID NO:2 and including at least one *B. lonestari* sp. nov.-specific amino acid or species-specific combination of amino acids from Table 1; and a second container means including a quantity of a detectably labelled antibody having binding specificity for the first antibody.

A further alternative is where a first container means includes a peptide epitope, the epitope being a partial or complete amino acid sequence of SEQ ID NO:2 and including at least one *B. lonestari* sp. nov.-specific amino acid or species-specific combination of amino acids from Table 1; and a second container means including a quantity of a detectably labelled antibody having binding specificity for immunoglobulin of the biological sample.

In these test kits, the detectably labelled antibody may be an enzyme-linked antibody, a fluorescently tagged antibody, or a radiolabeled antibody. Preferably, the detectably labelled antibody is an enzyme-linked antibody, and the kit further includes a third container means including a quantity of a substrate for the enzyme sufficient to produce a visually detectable product.

A diagnostic kit for determining the presence of *B. lonestari* sp. nov., in accordance with the present invention, may comprise any one or more of the following components:

1. Unique components in accordance with the present invention:
   a. An oligonucleotide complementary to a portion of the flagellin gene or the 16s rRNA gene at a region having a species-specific nucleotide or species-specific combination of nucleotides.
   b. Oligonucleotide primers for PCR™ designed to amplify a sequence of SEQ ID NO:1 or 3 where a first primer has a sequence 5' to a region of SEQ ID NO:1 or 3 having a species-specific nucleotide or species-specific combination of nucleotides and a second primer has a sequence 3' to the region. Primers may be designed to hybridize outside of the sequences depicted by SEQ ID NO: 1 or 3, since they may be complementary to vector sequences or naturally occurring flanking sequences, for example.
   c. A double stranded internal fragment of SEQ ID NO:1 or 3 provided for cloning and DNA sequencing to confirm the identity of a sequenced test fragment.
   d. DNA comprising the nucleic acid sequence of SEQ ID NO:1, 3 or 4 as a positive control template DNA for hybridization, sequencing, or RFLP analyses. This DNA may comprise plasmid DNA from clones described in Examples 2 and 3.
   e. Antibody having binding specificity for a *B. lonestari* flagellin species-specific epitope or species-specific combination of epitopes.
   f. A peptide having an amino acid sequence that includes a species-specific amino acid or species-specific combination of amino acids of Table 1.
2. Commercially available reagents:
   a. Components of a PCR™ reaction protocol.
   b. Components of a dideoxy-based sequencing protocol.
   c. Components of an ELISA protocol.

The following listing provides an identification of those sequences provided with sequence identifiers.

| Identity of Sequences having Sequence Identifiers | |
|---|---|
| SEQ ID NO: | Identity of Sequence |
| 1 | A composite sequence representing a partial nucleotide sequence of flagellin gene of new species |
| 2 | Partial amino acid sequence of flagellin protein of new species |
| 3 | Partial nucleotide sequence of 16s rRNA of new species |
| 4 | Partial nucleotide sequence of flagellin gene, initial fragment cloned and obtained by PCR ™ amplification, shorter than #1 |
| 5 | Species-specific epitope of flagellin at about amino acid 103 |
| 6 | Species-specific oligonucleotide of flagellin at about nucleotide 121 |
| 7 | Species-specific oligonucleotide of flagellin at about nucleotide 304 |
| 8 | Species-specific oligonucleotide of flagellin at about nucleotide 349 |
| 9 | FlaLS primer for PCR ™ |
| 10 | FlaRS primer for PCR ™ |
| 11 | FlaLL primer for PCR ™ |
| 12 | FlaRL primer for PCR ™ |
| 13 | 16RnaL primer for PCR ™ |
| 14 | 16RnaR primer for PCR ™ |
| 15–25 | Fragments of flagellin from various spirochetes for alignment purposes |
| 26 | Partial sequence of plasmid encoding fusion protein |
| 27 | N-terminal addition to flagellin protein in fusion construct after cleavage by protease |
| 28 | Partial nucleotide sequence of flagellin gene of clone 70 of a Texas tick of the new species; ATCC #, American Type Culture Collection, 12301 Parklawn Drive, Rockville, Maryland 20852 |

It will be understood that this invention is not limited to the exact nucleic acid and amino acid sequences described herein except for those species-specific nucleotides and amino acids and species-specific combinations of nucleotides and amino acids of Tables 1, 2 and 3. Therefore, DNA segments prepared in accordance with the present invention may also encode biologically functional equivalent proteins or peptides which have variant amino acid sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

The process of selecting and preparing a nucleic acid segment which includes a sequence from within SEQ ID NO:1 or 3 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,603,102 (incorporated herein by reference), by introducing selected sequences into recombinant vectors for recombinant production, and by other recombinant DNA techniques generally known to those of skill in the art of molecular biology.

BRIEF DESCRIPTION OF THE DRAWING

The following drawing forms part of the present specification and is included to further demonstrate certain aspects of the present invention. The invention may be better understood by reference to this drawing in combination with the detailed description of specific embodiments presented herein.

Figure 1:
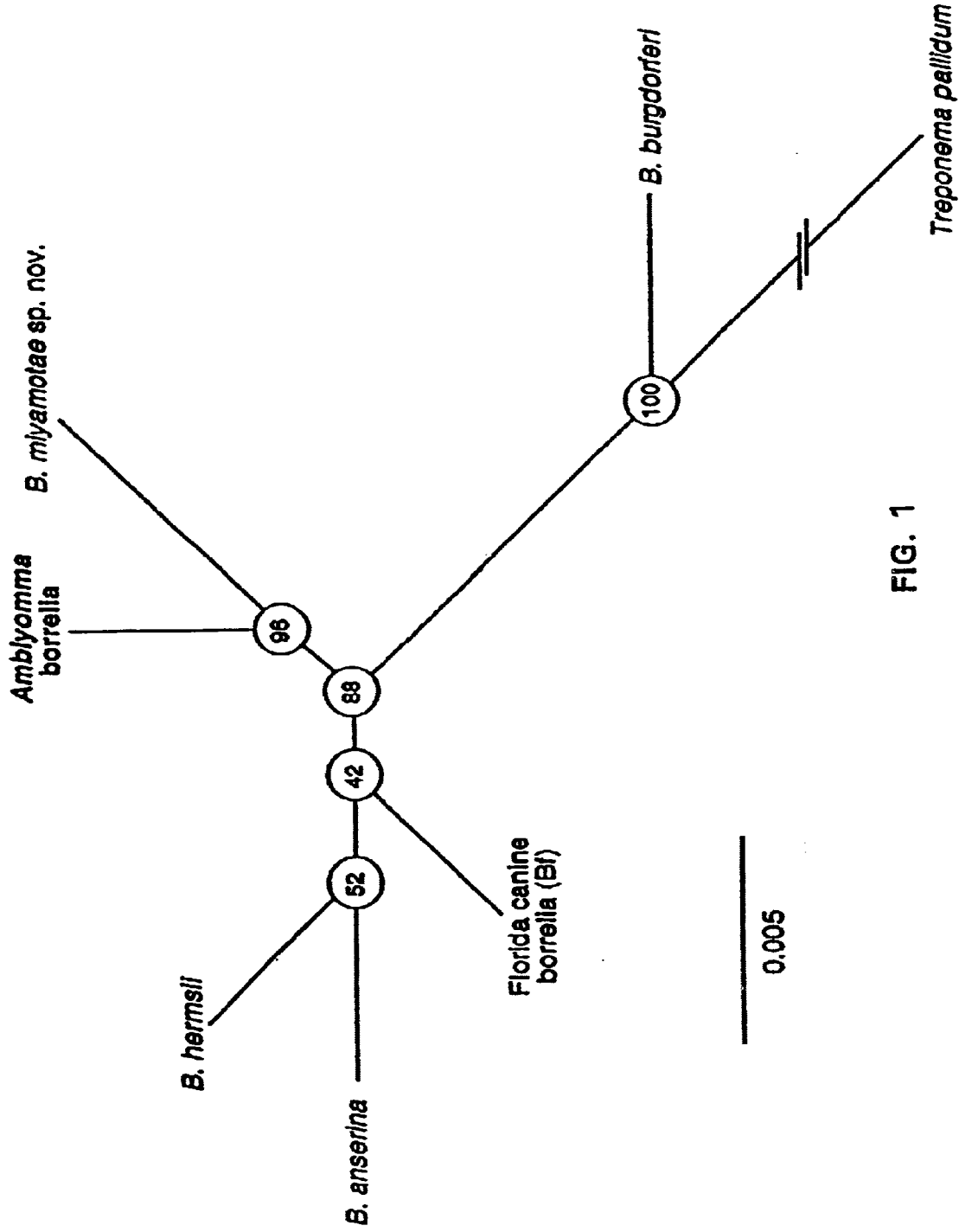
FIG. 1 shows a distance matrix phylogenetic tree of Borrelia spp. with *Treponema pallidum* as the outgroup. 16S rRNA sequences corresponding to base positions 36 through 1371 of *B. burgdorferi* rRNA gene (accession numbers U03396 and X57404) were aligned by the PileUp algorithm (Genetics Computer Group, Inc). Other sequences were *B. hermsii* (M60968 and L10136), *B. anserina* (M72397 and M64312), *B. miyamotae* sp. nov. (D45192), the "Florida canine borrelia" (L37837), and *T. pallidum* (M88726).

Aligned sequences were analyzed with the PHYLIP program package, version 3.5 (Felsenstein, 1989, 1993). Distance matrices were calculated with the Jukes-Cantor option of the DNADIST program. Multiple data sets were generated with SEQBOOT, unrooted trees were constructed using the NEIGHBOR program with the Neighbor-Joining option, and a consensus tree was generated with CONSENSE. Circles numbers indicate the number of times out of 100 that a particular node was supported by bootstrap analysis. Approximate evolutionary distances are measured along line segments; the bar represents a distance by Jukes-Cantor criteria of 0.005. The calculated distances of the Amblyomma borrelia from *B. hermsii*, *B. burgdorferi*, and *T. pallidum* were 0.022, 0.041, and 0.233, respectively. Tree topology was also examined by subjecting the 100 bootstrapped datum sets to parsimony analysis with the DNAPARS algorithm. The consensus treefile (New Hampshire Standard format) from the parsimony analysis was: (Amblyomma borrelia: 100, *B. miyamotae*: 100): 94, *B. hermsii*: 100): 34, Florida canine borrelia: 100): 25, *B. anserina* 100): 81, *B. burgdorferi*: 100): 100, *T. pallidum*: 100).

DETAILED DESCRIPTION OF THE PREFERRED EMBODIMENTS

The newly recognized tick-borne disease in Texas, Missouri, and states in the south central and southeastern United States is similar to Lyme disease in many respects but cannot be distinguished from Lyme disease by visual inspection of the rash, for example. Another Borrelia disease that is difficult to distinguish from Lyme disease, using the standard laboratory test for Lyme disease, is relapsing fever which is associated with bites from Ornithodoros spp. ticks.

The present invention provides diagnostic tests based on species-specific regions or species-specific combination of regions of the flagellin protein, the flagellin gene, or the 16s rRNA of the new spirochete, named by the present inventors as *Borrelia lonestari* sp. nov. The flagellin protein is sufficiently different from other Borrelia spp. that a serodiagnostic assay based on flagellin antigen (recombinant, synthetic, or native) is both sensitive and specific for putative infections. The DNA sequences of both the flagellin gene and the rRNA gene provide a means for PCRM and other nucleic acid-based technologies to identify the organism from skin, body fluid, or cellular specimen of a person, animal, insect and the like, suspected of being infected. Animal reservoirs that are particularly suspect include deer and ground-feeding birds. The diagnostic tests provided herein provide clinical laboratory differentiation of the new tick-borne disease from the causative agents of Lyme disease and relapsing fever. The demonstration of *B. lonestari* sp. nov. in humans provides the basis for a diagnosis of infection by this new spirochete.

*B. lonestari* sp. nov.-Species-Specific Amino Acid(s) and Species-Specific Combinations of Amino Acid(s) from the Flagellin Protein A preferred embodiment of the present invention is a purified composition comprising a polypeptide having an amino acid sequence in accordance with SEQ ID NO:2. The term "purified" as used herein, is intended to refer to a flagellin protein composition, wherein the flagellin protein is purified to any degree relative to its naturally-obtainable state, i.e., in this case, relative to its purity as part of a Borrelia cell extract. A preferred cell for the isolation of flagellin protein is a *B. lonestari* sp. nov. cell, however, this flagellin protein may also be isolated from the *A. ameri-canum* tick, patient specimens, recombinant cells, tissues, and the like, as will be known to those of skill in the art, in light of the present disclosure. A purified flagellin protein composition therefore also refers to a polypeptide comprising the amino acid sequence of SEQ ID NO:2, free from the environment in which it may naturally occur. The flagellin protein may be purified by a procedure of Barbour et al. (1986), for example.

The present inventors have prepared and envision the preparation of various fusion proteins and peptides, e.g., where species-specific flagellin gene coding regions or species-specific combination of flagellin gene coding regions are aligned within the same expression unit with nucleotide sequences encoding other proteins or peptides having desired functions, such as for purification or immunodetection purposes (e.g., proteins which may be purified by affinity chromatography and enzyme label coding regions, respectively).

Table 1 provides a listing of those species-specific amino acids and species-specific combinations of amino acids of the partial sequence of the flagellin protein of *B. lonestari* sp. nov. provided as SEQ ID NO:2. These amino acids or species-specific combinations thereof represent variations in their respective positions compared to the corresponding available sequences of other Borrelia species.

The species-specific amino acids or species-specific combination of amino acids of this new spirochete provide unique epitopes for assay for identification of the organism. Two types of immunoassay are contemplated: i) the first uses an epitope comprising a peptide having a sequence represented in SEQ ID NO:2 and containing a *B. lonestari* sp. nov.-specific amino acid(s) or species-specific combination of amino acids of Table 1 to assay for the presence of antibodies having specificity for that epitope in a clinical sample and, ii) the second type of immunoassay uses antibodies that have been raised to such an epitope to assay for the presence of the epitope in the clinical sample.

An epitope useful for immunoassay contains at least one of the *B. lonestari* sp. nov.-specific amino acids or species-specific combination of amino acids of Table 1 together with at least about 4, 5, or 6 amino acids that flank that amino acid(s) in the flagellin protein sequence designated SEQ ID NO:2. Where the uniqueness of the flagellin protein is due to a deletion of residues compared to other Borrelia species, then the epitope contains at least two, and preferably 3 or 4 amino acids from that region of SEQ ID NO:2 as cited in Table 1 and is flanked with further amino acids on both. sides of the epitope from SEQ ID NO:2. Such peptide epitopes may be made synthetically, or may be isolated from natural sequences by enzyme digestion, for example, or may be produced by recombinant means, described more fully herein.

As used herein, "an epitope useful for immunoassay" refers to a peptide or protein antigen which includes a primary, secondary or tertiary structure similar to an epitope comprising a *B. lonestari* sp. nov.-specific amino acid(s) or species-specific combination of amino acids of Table 1 located within the flagellin protein of *B. lonestari* sp. nov. The level of similarity will generally be to such a degree that monoclonal or polyclonal antibodies directed against the *B. lonestari* sp. nov. flagellin protein will bind to, react with, or otherwise recognize, the peptide or protein antigen.

In general, the size of the polypeptide epitope is at least large enough to carry an identified *B. lonestari* sp. nov.-specific amino acid or species-specific combination of amino acids of Table 1. The smallest useful core sequence contemplated by the present disclosure would generally be on the order of about 6 amino acids in length. Thus, this size will generally correspond to the smallest peptide antigens prepared in accordance with the invention. It is proposed that short peptides that incorporate a species-specific amino acid or species-specific combination of amino acids of Table 1 will provide advantages in certain circumstances, for example, in the preparation of vaccines or in immunologic detection assays. Exemplary advantages of shorter peptides include the ease of preparation and purification, and the relatively low cost and improved reproducibility of production. However, the size of the epitope may be larger where desired, so long as it contains a peptide sequence of SEQ ID NO:2 having a B. lonestari sp. nov.-specific amino acid or species-specific combination of amino acids of Table 1. Longer peptide epitopes for use in accordance with the present invention will generally be on the order of 15 to 30 amino acids in length, and more preferably about 15 to about 50 amino acids in length.

Additionally or alternatively, an epitopic sequence of the present invention is one that elicits antibodies that react with B. lonestari sp. nov. flagellin protein of SEQ ID NO:2 and the antibodies do not cross-react with flagellin protein from other Borrelia species. Thus, epitope sequences of the present invention may be operationally defined in terms of their ability to compete with or perhaps displace the binding of the peptide of SEQ ID NO:2 with the corresponding flagellin-directed antisera.

Syntheses of epitopic peptides are readily achieved using conventional synthetic techniques such as the solid-phase method (e.g., through the use of commercially available peptide synthesizer such as an Applied Biosystems Model 430A Peptide. Synthesizer). Peptide epitopes synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated, it will generally be desirable to include agents including buffers such as Tris or phosphate buffer to maintain a pH of 7.0 to 7.5. Moreover, it may be desirable to include agents which will inhibit microbial growth, such as sodium azide or merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

Peptides may be labeled with $^{125}$I, $^{131}$I, or other radiolabel as a means for detection, or may be labeled with a chromophore, such as, for example, biotin, HRP, or alkaline phosphatase, for detection.

Antibodies

In another aspect, the present invention contemplates an antibody that is immunoreactive with an epitope having a sequence of SEQ ID NO:2 containing a B. lonestari sp. nov.-specific amino acid(s) or species-specific combination of amino acids of Table 1. An antibody can be a polyclonal or a monoclonal antibody. In a preferred embodiment, an antibody is a monoclonal antibody. Means for preparing and characterizing antibodies are well known in the art (See, e.g., Antibodies "A Laboratory Manual, E. Howell and D. Lane, Cold Spring Harbor Laboratory, 1988).

Briefly, a polyclonal antibody is prepared by immunizing an animal with an immunogen comprising an epitope of the present invention and collecting antisera from that immunized animal. A wide range of animal species can be used for the production of antisera. Typically an animal used for production of anti-antisera is a rabbit, a mouse, a rat, a hamster, a guinea pig, or a goat. Because of the relatively large blood volume of goats and rabbits, a goat or rabbit is a preferred choice for production of polyclonal antibodies.

Antibodies, both polyclonal and monoclonal, specific for an epitope of the present invention may be prepared using conventional immunization techniques, as will be generally known to those of skill in the art. A composition comprising an epitope having a sequence represented in SEQ ID NO:2 and containing a B. lonestari sp. nov.-specific amino acid or species-specific combination of amino acids of Table 1 can be used to immunize one or more experimental animals, such as a rabbit or mouse, which will then proceed to produce specific antibodies against the peptide epitope. Polyclonal antisera may be obtained, after allowing time for antibody generation, simply by bleeding the animal and preparing serum samples from the whole blood.

To obtain monoclonal antibodies, one would also initially immunize an experimental animal, preferably a mouse, with the above-described composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired species-specific epitope or species-specific combination of epitopes of B. lonestari sp. nov.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against a species-specific epitope or species-specific combination of epitopes. Hybridomas which produce monoclonal antibodies to the species-specific epitope or species-specific combination of epitopes are identified using standard techniques, such as ELISA and Western blot methods.

Hybridoma clones can then be cultured in liquid media and the culture supernatants purified to provide the B. lonestari sp. nov.-specific monoclonal antibodies. In general, for uses in accordance with the present invention, one will preferably desire to select those hybridomas that secrete antibodies having a high affinity for the species-specific epitopes or species-specific combination of epitopes of flagellin protein, and exhibit minimal binding to other Borrelia species flagellin protein.

Monoclonal antibodies to the desired B. lonestari sp. nov.-specific flagellin epitopes or species-specific combination of flagellin epitopes can be used in the diagnosis of infections caused by the Amblyomma tick and that are Lyme disease-like but test negative for Lyme disease.

It is proposed that the monoclonal antibodies of the present invention will find useful application in standard immunochemical procedures, such as ELISA and Western blot methods, as well as other procedures, such as immunohistology of tissues, that may utilize antibody specific to the species-specific epitopes or species-specific combination of epitopes of the present invention. Additionally, species-specific monoclonal antibodies may be useful in immunoadsorbent protocols for purifying native or recombinant *B. lonestari* sp. nov. flagellin protein or minor variants thereof.

Both poly- and monoclonal antibodies may be employed in antibody cloning protocols to obtain genes encoding *B. lonestari* sp. nov. flagellin or related proteins. Species-specific anti-flagellin antibodies will also be useful in immunolocalization studies to analyze the distribution of flagellin protein during various cellular events, for example, to determine the cellular and membrane distribution during flagella assembly. A particularly useful application of such antibodies is in purifying native or recombinant flagellin protein, for example, using an antibody affinity column. The operation of all such immunological techniques will be known to those of skill in the art in light of the present disclosure.

Immunoassays

The present invention envisions the use of immunoassays for the detection of *B. lonestari* sp. nov.-specific epitopes or species-specific combination of epitopes for the diagnosis of the presence of *B. lonestari* sp nov. Various immunoassay methods may be employed, such as, for example, Western blotting, ELISA, RIA, and the like, all of which are known to those of skill in the art.

Enzyme linked immunoadsorbent assays (ELISAS) may be used in conjunction with the invention. In an ELISA assay, proteins or peptides incorporating species-specific sequences or species-specific combination of sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera.is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing; the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-appropriate-animal IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

The antibody compositions of the present invention find great use in immunoblot or Western blot analysis. The antibodies may be used as high affinity primary reagents for the identification of proteins immobilized onto a solid support matrix, such as nitrocellulose, polyacrylamide, nylon, or the like. In conjunction with gel electrophoresis and immunoprecipitation, the antibodies may be used as a single step reagent for use in detecting species-specific epitopes of *B. lonestari* sp. nov. Immunologically-based detection methods for use in conjunction with Western blotting include enzymatically-, radiolabel-, or fluorescently-tagged secondary antibodies against the primary antibody moiety are considered to be of particular use in this regard.

Other methods for detection of antigens and antibodies well known in a clinical laboratory setting are contemplated by the present invention, including: immunodiffusion, electrophoresis and immunoelectrophoresis, immunochemical and physicochemical methods, binder-ligand assays, immunohistochemical techniques (immunofluorescence), agglutination, IgG and IgM capture assay test, competitive inhibition assays for antibodies, or complement assays.

Immunodetection Kits

In still further embodiments, the present invention concerns immunodetection methods and associated kits. It is proposed that the *B. lonestari* sp. nov.-specific peptides or species-specific combination of peptides of the present invention may be employed to detect antibodies having reactivity therewith, or, alternatively, antibodies prepared in accordance with the present invention, may be employed to detect species-specific proteins or peptides or species-specific combinations thereof. In general, these methods will include first obtaining a sample suspected of containing such a protein, peptide or antibody, contacting the sample with an antibody or species-specific protein or peptide or species-specific combination of protein or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot, dot blot, indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising either the species-specific protein or peptide or antibody sought to be detected as the case may be, may be employed. Exemplary samples include the tick suspected of harboring the new Borrelia species, and clinical samples obtained from a patient such as blood or serum samples, a skin biopsy, cerebrospinal fluid, or urine samples. For antigen or DNA testing, a blood, CSF, or urine sample is preferred. A preferred sample for antibody tests is a blood or CSF sample. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of species-specific proteins or peptides and/or antibodies in a sample. Generally speaking, kits in accordance with the present invention will include a suitable *B. lonestari* sp. nov.-specific protein or peptide, or species-specific combination thereof, or antibody directed against such a protein or peptide or species-specific combination thereof, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

B. lonestari sp. nov.-Specific Nucleotides and Species-Specific Combination of Nucleotides of the flagellin and 16s rRNA Genes.

Further preferred embodiments of the present invention include a purified composition comprising a nucleic acid having a nucleotide sequence in accordance with SEQ ID NOS:1, 3 or 4. The term "purified" as used herein, is intended to refer to a nucleic acid composition, in this case, a flagellin gene or segment thereof, or a rRNA gene or segment thereof, wherein the nucleic acid is purified to any degree relative to its naturally-obtainable state, i.e., in this case, relative to its purity as part of a Borrelia cell extract. A preferred cell for the isolation of this nucleic acid is a *B. lonestari* sp. nov. cell, however, this nucleic acid may also be isolated from the *A. americanum* tick, patient specimens, recombinant cells, tissues, and the like, as will be known to those of skill in the art, in light of the present disclosure. A purified nucleic acid composition therefore also refers to a nucleic acid comprising the nucleotide sequence of SEQ ID NO:1, 3 or 4, free from the environment in which it may naturally occur.

The present inventors have prepared and envision the preparation of various recombinant products comprising nucleotide segments representing whole or partial sequences of SEQ ID NO:1, 3 or 4, e.g., where species-specific flagellin gene coding regions or species-specific combination(s) of flagellin gene coding regions are aligned within the same expression unit with nucleotide sequences encoding other proteins or peptides to construct a fusion protein as herein described. Recombinant products include the vectors themselves, including, for example, plasmids, cosmids, phage, viruses, and the like. It will be understood that the present invention also encompasses sequences which are complementary to the sequences listed herein, along with biological functional equivalents thereof, including naturally occurring variants and genetically engineered mutants.

As used herein, the term "recombinant" is intended to refer to a vector or host cell into which a foreign piece of DNA, such as a gene encoding a *B. lonestari* sp. nov. nucleic acid, has been introduced. Therefore, engineered cells are distinguishable from naturally occurring cells that do not contain a recombinantly introduced gene. Engineered cells are thus cells having a gene or genes introduced through the hand of man. Recombinantly introduced genes will either be in the form of a copy of a genomic gene, or will include genes positioned adjacent to a promoter not naturally associated with the particular introduced gene.

Prokaryotic hosts may be used for expression of a *B. lonestari* sp. nov. protein. Some examples of prokaryotic hosts are: *E. coli*, such as for example, strain RR1, *E. coli* LE392, *E. coli* B, *E. coli* X 1776 (ATCC No. 31537, American Type Culture Collection, 12301 Parklawn Drive, Rockville, M.d. 20852) as well as *E. coli* W3110 (F-, lambda-, prototrophic, ATCC No. 273325, American Type Culture Collection, 12301 Parklawn Drive, Rockville, M.d. 20852); other enterobacteriaceae such as *Salmonella typhimurium* or *Serratia marcescens*; bacilli such as *Bacillus subtilis*; various Pseudomonas species, Mycobacterium species such as bovis, Streptomyces species, or Clostridium species may be used.

In general, plasmid vectors containing replicon and control sequences that are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Those promoters most commonly used in recombinant DNA construction include the B-lactamase (penicillinase), lactose promoter systems, and a tryptophan (trp) promoter system. While these are the most commonly used, other microbial promoters have been discovered and utilized, and details concerning their nucleotide sequences have been published, enabling a skilled worker to ligate them functionally with plasmid vectors (Sambrook et al., 1989).

It is similarly believed that almost any eukaryotic expression system may be utilized for the expression of the flagellin gene; e.g., Saccharomyces, Baculovirus, SV40, Adenovirus, glutamine synthase-based or dihydrofolate reductase-based systems could be employed. For example, plasmid vectors incorporating an origin of replication and an efficient eukaryotic promoter will be of most use. Advantages of a eukaryotic expression system include the ease of producing a large amount of protein and avoidance of contamination with any bacterial products that may be bound by antibodies in sera.

For expression in this manner, one would position the coding sequences adjacent to and under the control of the promoter. It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the flagellin gene, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Table 2 provides a listing of those *B. lonestari* sp. nov.-specific nucleotides and species-specific combination(s) of nucleotides of the flagellin gene of *B. lonestari* sp. nov. These nucleotides represent variations in their respective positions compared to the corresponding available sequences of other Borrelia species.

Table 3 provides a listing of those species-specific nucleotides and species-specific combination(s) of nucleotides of the 16s rRNA gene of *B. lonestari* sp. nov. These nucleotides represent variations in their respective positions compared to the corresponding available rRNA sequences of other Borrelia species.

The *B. lonestari* sp. nov.-specific nucleotides or species-specific combination of nucleotides of this new spirochete, both from the flagellin and the rRNA genes, provide uniqae nucleotide targets for assay for identification of the organism. Nucleotide assays that are contemplated include:

i) For both the flagellin and rRNA genes, the nucleotide sequence of a segment containing any of the species-specific nucleotides or species-specific combination of nucleotides of Tables 2 or 3 clearly determines the identity of the sample being examined. A region containing the species-specific nucleotides or species-specific combination of nucleotides would be amplified by a polymerase chain reaction (PCR™) and used for standard nucleotide sequence analysis as described in Example 2 and 3.

ii) For the flagellin gene, hybridization of species-specific oligonucleotide probes to a sample being analyzed will identify the sample. The species-specific nucleotide probe would be complementary to and would hybridize with areas of the nucleotide sequence provided in SEQ ID NO:1 having a species-specific nucleotide or species-specific combination of nucleotides as shown in Table 2. Preferred nucleotide probes would be complementary to and, therefore, hybridize with those regions of the *B. lonestari* sp. nov. sequence that are species-specific due to deletions of nucleotides from the flagellin gene of related Borrelia species (Table 2).

iii) Restriction fragment length polymorphism analysis of a sample of DNA from an infected human, or DNA from a tick or the spirochete will determine identity of the Borrelia species.

Each of these nucleotide assay embodiments is discussed in further detail as follows.

PCR™ Amplification and DNA Sequence Analysis

DNA primers that would be useful in PCR™ may be derived from any portion of SEQ ID NOS:1 or 3 as long as one primer is 5' to a species-specific nucleotide or species-specific combination of nucleotides and a second primer is 3' to the same species-specific nucleotide or combination. PCR™ primers generally are about at least 13 nucleotides in length and may be up to 20 or 25 or 30 nucleotides or even longer, and the region primed and amplified may range from about 50 nucleotides to about 2000 nucleotides. A preferred amplified product is about 100 to 300 or 400 nucleotides long.

Nucleic acid sequencing is carried out using the dideoxy chain termination technique (Sanger et al., 1977, and Sambrook et al., 1989). One skilled in this art would be familiar with the PCR™ amplification procedure and nucleic acid sequencing and would know, in light of the present disclosure, how to use the sequences provided herein to amplify regions of the flagellin gene and the rRNA gene to obtain PCR™ products for nucleotide sequencing. Examples of these procedures are provided in Examples 2 and 3.

Oligonucleotide Probes for Hybridization

An oligonucleotide probe of the present invention for hybridization to determine identity of a clinical sample is a nucleotide sequence of SEQ ID NO:1 that is complementary to a region of the flagellin gene having a *B. lonestari* sp. nov.-specific nucleotide or species-specific combination of nucleotides of Table 2 within that region. One skilled in this art would also realize that the complement of the oligonucleotide would also detect that region of sequence by binding to the opposite strand of DNA.

The probe may be from about 13 nucleotides in length up to and including the full length sequence, preferably is about 13–30 nucleotides in length and is most preferably from about 15 to about 18, 19, 20 or 21 nucleotides in length. The oligonucleotide binds to its complement under standard hybridization conditions. The term "standard hybridization conditions" as used herein, is used to describe those conditions under which substantially complementary nucleic acid segments will form standard Watson-Crick base-pairing. A number of factor are known that determine the specificity of binding or hybridization, such as pH, salt concentration, the presence of chaotropic agents (e.g. formamide and dimethyl sulfoxide), the length of the segments that are hybridizing, and the like.

For use with the present invention, standard hybridization conditions for relatively large segments, that is segments longer than about 100 nucleotides, will include a hybridization mixture having between about 0.3 to 0.6 M NaCl, a divalent cation chelator (e.g. EDTA at about 0.05 mM to about 0.5 mM), and a buffering agent (e.g. $Na_2PO_4$ at about 10 mM to 100 mM, pH 7.2), at a temperature of about 65° C. The preferred conditions for hybridization are a hybridization mixture comprising 0.5 M NaCl, 5 mM EDTA, 0.1 M $Na_2PO_4$, pH 7.2 and 1% N-lauryl sarcosine, at a temperature of 65° C. Naturally, conditions that affect the hybridization temperature, such as the addition of chaotropic agents, such as formamide, will be known to those of skill in the art, and are encompassed by the present invention.

When it is contemplated that shorter nucleic acid segments will be used for hybridization, for example fragments between about 15 and about 30 nucleotides, salt and temperature conditions will be altered to increase the specificity of nucleic acid segment binding. Preferred conditions for the hybridization of short nucleic acid segments include lowering the hybridization temperature to about 37° C., and increasing the salt concentration to about 0.5 to 1.5 M NaCl with 1.5 M NaCl being particularly preferred.

For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for a diagnostic assay.

Oligonucleotides for use as probes may be readily prepared by, for example, directly synthesizing the fragment by chemical means, by application of nucleic acid reproduction technology, such as the PCR™ technology of U.S. Pat. Nos. 4,683,202 and 4,683,195 (herein incorporated by reference) or by introducing selected sequences into recombinant vectors for recombinant production.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, that are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in esolution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

Restriction Fragment Length Polymorphism

Analyses of the sequence provided in SEQ ID NOS:1 and 3 indicate that different patterns of products are found when the B. lonestari sp. nov. DNA is cleaved by a restriction enzyme compared to the restriction patterns obtained from other species of Borrelia. In particular, as shown in Example 2, an AluI digest of an about 330 bp PCR™ product (SEQ ID NO:4) and electrophoretic analysis of the enzyme digest yielded characteristic restriction fragments for different species of Borrelia, including B. burgdorferi B31, from two North American relapsing fever agents B. hermsii HS1 and B. turicatae "Ozona", and from immunofluorescence-positive Amblyomma ticks from Texas and New Jersey. The gel patterns of the two Amblyomma tick samples both differed from the digested products from B. burgdorferi, B. hermsii, and B. turicatae. Further enzyme digests that demonstrate polymorphisms are shown in Table 7 of Example 5. DNA is prepared from a sample for RFLP analysis as described in Examples 2 and 3. Primers are hybridized to the DNA and the PCR™ reaction carried out also substantially as described in those examples. One skilled in the art would know that other primers may be used, especially if the DNA fragment to be amplified is cloned into a vector of known sequence. A restriction enzyme digest is carried out choosing from those enzymes of Table 7, and the digest applied to, preferably, an agarose gel. Visualization of the restriction enzyme fragments and comparison of their sizes with those listed in Table 7 provide identification of the Borrelia species.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Evidence for a Spirochete in A. americanum That Cross-Reacts With Anti B. Burgdorrei Antiserum The present example provides evidence for a spirochete in A. americanum that cross-reacts with anti-B. Burgdorfei antiserum at high concentrations of the antiserum.

For the present study, A. americanum ticks were collected from field locations in Missouri, New Jersey, New York, North Carolina, and Texas and examined with anti-B. burgdorferi polyclonal antisera in concentrations giving cross-reactions with other Borrelia spp. (Maupin et al., 1991). Fluorescent photomicrographs were taken of B. turicatae, a relapsing fever agent, and spirochetes in the crushed midgut of an A. americanum tick stained with a 1:10 dilution of fluorescein isothiocyanate-conjugated rabbit antibodies to B. burgdorferi (Maupin et al., 1991). Approximately 2% of the ticks, both nymphs and adults, in Missouri, New Jersey, New York, and North Carolina contained immunoreactive spirochetes of between 10 and 20 μm in length as shown in Table 4. The results for the Texas organisms were similar.

TABLE 4

Presence of immunofluorescence-reactive spirochetes in Amblyomma americanum nymphal and adult ticks*

| LOCATION | # POSITIVE(adults) | # EXAMINED (adults) |
|---|---|---|
| Monmouth Co., NJ | 3 (2) | 110 (50) |
| Suffolk Co., NY | 10 (9) | 375 (318) |
| Currituck Co., NC | 1 (0) | 95 (26) |
| Southeast MO† | 6 (0) | 295 (29) |
| Total | 20 (11) | 875 (423) |
| % positive [range] | 2.3% [1.1–2.7%] | |

*Reactive with 1:10 dilution of fluorescein-conjugated antiserum to B. burgdorferi (Maupin et al., 1991). The spirochete was not detected with a 1:100 dilution of the antiserum.
†Bollinger Co., Pulaski Co., and Stoddard Co., MO To characterize the A. americanum spirochete, attempts were made to cultivate it in media that supports the growth of several Borrelia spp., including those that cause Lyme disease and several that cause relapsing fever (Barbour, 1984). In addition, some samples with the suspected agent were injected into laboratory mice, which were subsequently examined for illness and their organs were cultured. These attempts, like those in the past (Schulze et al., 1984; Kocan et al., 1992), failed to isolate the organism in the laboratory.

EXAMPLE 2

The *A. americanum* Spirochete is a New Borrelia Species, *B. lonestara* sp. nov.

The present example describes the inventors' analysis of the *A. americanum* spirochete that led to their determination that the spirochete is a new Borrelia species.

The present inventors used the polymerase chain reaction (PCR™) and amplification of conserved genes using primers designed on the basis of sequences of possibly-related organisms (Relman, 1993). The genes for 16S rRNA and flagellin, the major structural protein of flagella, of several Borrelia spp. were available, and alignment revealed regions of genus-specific sequences.

*A. americanum* ticks were collected in New Jersey and New York from the field by flagging. Flagging is a technique described in Maupin et al., (1991) which reference is specifically incorporated herein by reference. *A. americanum* ticks from Texas had been removed from human hosts and submitted to the Department of Health. Ticks were dissected with sterile instruments, and portions of their midguts were examined by direct fluorescent microscopy with polyclonal antiserum to *B. burgdorferi* (Maupin et al., 1991). DNA from positive and negative ticks was extracted at two locations using different extraction methods: (a) Ticks from New York and New Jersey were individually placed in sterile plastic bags, frozen, and crushed. To the homogenate was added, first, 0.5 ml of 10 mM Tris, pH 8.0–1 mM EDTA (TE) with 0.1 mg/ml of yeast tRNA and 1% sodium dodecyl sulfate (SDS) and, then, 0.5 ml of phenol. The aqueous phase was extracted with ether. (b) Ticks from Texas were placed in sterile microfuge tubes. To the tube was added 0.2 ml of 10 mM Tris, pH 8.0–50 mM EDTA-2% SDS. The suspension was heated to 64° C. for 20 min, extracted with phenol, and twice with chloroform. The DNA obtained by both methods was precipitated with ethanol and resuspended in TE. The investigator who performed the PCR™ was blind to the findings of the tick examinations.

The sequence of a first set of PCR™ primers (FlaLS and FlaRS) was based on identical sequences in flagellin of Borrelia spp. The positions listed in parentheses following the sequence refer to *B. burgdorferi* flagellin (Fla) gene: FlaLS: 5'AACAGCTGAAGAGCTTGGAATG3' (438–459); SEQ ID NO:9 FlaRS: 3'CGATAATCTTACTAT-TCACTAGTTTC5' (766–791); SEQ ID NO:10. The primers differed in sequence at two or more positions from homologous sequences of other spirochetes and bacteria. This first set of primers was expected to amplify a ~330 base-pair fragment of the flagellin gene of any Borrelia spp.

PCR™ primers were synthesized as follows. PCR™ reactions in volumes of 100 μl containing 2.5 U of Taq DNA polymerase (Boehringer-Mannheim), 50 pmole of each primer, 200 μM of each dNTP, 10 mM Tris (pH 8.3), 50 mM KCl, 1.5 mM $MgCl_2$, and 0.001% gelatin were carried out in Perkin-Elmer-Cetus thermal cycler. The reaction program was first 95° C. for 3 min and then 40 cycles of 95° C. for 1 min, 55° C. for 1 min., and 75° C. for 1 min.

Subsequent AluI restriction enzyme digestion of the PCR™ products and electrophoretic analysis of the enzyme digest (4% NuSieve™ gel, FMC, (Rockland, Me.) with Tris-acetate-EDTA buffer) yielded characteristic restriction fragments for different species of Borrelia, including *B. burgdorferi* B31, from two North American relapsing fever agents *B. hermsii* HS1 and *B. turicatae* "Ozonall", and from immunofluorescence-positive Amblyomma ticks from Texas and New Jersey. The gel patterns of the two Amblyomma tick samples revealed fragments of about 117, 85 and 55 base pairs; from *B. burgdorferi*, about 130 and 106 base pairs; from *B. hermsii*, about 160, 100 and 75 base pairs; and from *B. turicatae*, about 110 and 75 base pairs.

PCR™ products from one of the Texas ticks and one of the New Jersey ticks were cloned into vector pCRII™ using the TA Cloning System and *E. coli* strain INVαF' (Invitrogen, San Diego, Calif.). Sequences of both strands from at least two clones of each PCR™ product were determined from double-stranded DNA using SEQUE-NASE™ version 2.0 (U.S. Biochemical, Amersham Life Sci, Arlington Heights, Ill.) and custom-synthesized primers. The sequence of this ~330 base region is provided as SEQ ID NO:4. Both sequences were confirmed to be the central portion of a flagellin gene, but they were not identical to comparable regions of other Borrelia spp. flagellin genes in the sequence databases (see Example 3).

To assess the specificity of the PCR™ reaction, additional extracts from *A. americanum* ticks from New York were examined. For this study, extracted DNA was subjected to PCR™ with primer pairs FlaSL and FlaSR. The PCR™ products were subjected to Southern blot analysis by separating the products in a 0.9% GTG™ agarose gel (FMC) in Tris-borate-EDTA buffer, and, after transfer to 0.22 mm Nytranm membranes (Schleicher & Schuell, Keene, N. H.), probed with the PCR™ product from the Texas tick. The probe was labeled with [$^{32}$P]-dATP using a nick translation kit (Gibco/BRL, Gathersburg, Md.). Prehybridization was carried out in hybridization medium (6×SSC, 5×Denhardt's, 0.5% SDS, 100 μg/ml denatured salmon sperm DNA, 50% formamide to 200 ml with water) for 1–4 h at 37°. The probe was added and hybridization was carried out overnight at 37°. The first and second washes were with 2×SSC, 0.1 SDS, 1 mM EDTA, for 5 min at room temperature. The third and fourth washes were with 100–200 ml of 0.1×SSC, 0.1% SDS, 1 mM EDTA, for 15–30 min at 64° C. The final wash was with 0.1×SSC at room temperature. X-ray film was exposed with an intensifying screen. Nine of 10 extracts from ticks that were positive by direct fluorescence assay with conjugated rabbit antibody to *B. burgdorferi* (Maupin et al., 1991) had products that detectably hybridized with the probe; none of 11 ticks that were negative by the direct fluorescence assay hybridized with the probe (p<0.0001 by two-tailed Fisher exact test). This test indicates that the DNA obtained by the PCR™ reaction was specific for anti-Borrelia-positive spirochetes. This new Borrelia species was named *B. lonestari* sp. nov. The anti-*B. burgdorferi* antibody, at high concentrations, cross-reacts with all Borrelia species, whereas a DNA probe of the present invention is expected to bind only *B. lonestari* sp. nov. samples.

EXAMPLE 3

Regions of *B. lonestari* sp. nov. Flagellin Gene and rRNA Gene Sequences Differ From Those of Other Borrelia sp.

The present example describes those regions of the *B. lonestari* sp. nov. flagellin amino acid and rRNA sequences that differ from those of other Borrelia sp.

With the inventors' collection of evidence that the Amblyomma spirochete was a new Borrelia sp., sets of primers were used to amplify a larger region of the flagellin gene and most of the 16S rRNA gene. The primers were based on identical sequences in flagellin and 16S rRNA genes of Borrelia spp. The primers differed in sequence at two or more positions from homologous sequences of other spirochetes and bacteria. In the following primer sequences, the positions listed in parentheses refer to *B. burgdorferi* flagellin (Fla) and 16S rRNA (16Rna) genes:

FlaLL, 5'ACATATTCAGATGCAGACAGAGGT3' (301–324); SEQ ID NO:11

FlaRL, 3'TGTTAGACGTTACCGTTACTAACG5' (942–965); SEQ ID NO:12

16RnaL, 5'CTGGCAGTGCGTCTTAAGCA3' (36–55); SEQ ID NO:13

16RnaR, 3'CATATAGTCTTACTATGCCACTTAG5' (1346–1368). SEQ ID NO:14 PCR™ primers were synthesized as described in Example 2.

PCR™ products from organisms in ticks from Texas and New Jersey were sequenced over both strands and as different recombinant clones. PCR™ products were obtained with primer pairs FlaLS+FlaRS, FlaLL+FlaRL, and 16RnaR+16RnaL and cloned into vector pCRII™ using the TA Cloning System and *E. coli* strain INVaF' (Invitrogen). Sequences of both strands from at least two clones of each PCR' product were determined from double-stranded DNA using Sequenase version 2.0 (U. S. Biochemical) and custom-synthesized primers. The nucleotide sequence of the flagellin fragment is assigned SEQ ID NO:1 and contains about 70% of the flagellin gene; the deduced amino acid sequence is assigned SEQ ID NO:2. This fragment contains the variable portion of the sequence of bacterial flagellin genes and is the region that contains species-specific epitopes or species-specific combination of epitopes of the flagellin protein.

Three PCR™ clones of the Texas tick, positioned in the vector pCRII™ and in the host *E. coli* strain INVαF' (Invitrogen), were sequenced for comparison to neutralize errors made by the polymerase enzyme in this method. These clones are designated as follows: i) clone 70, named pTxfla70, deposited with the American Type Culture Collection, 12301 Parklawn Drive, Rockville, Md. 20852 as ATCC#; the sequence from this tick is SEQ ID NO: 28 and has a "A" at position 345 instead of a "G" as shown in SEQ ID NO: 1; ii) clone 69 which has an "A" at position 345, a "C" at position 573, and a "T" at position 586 compared to SEQ ID NO: 1; and iii) clone 5 which has a "T" at position 3, and a "T" missing at position 24 compared to SEQ ID NO: 1. A composite sequence, obtained by comparison of these clones, and comparison with other Borrelia sequences, is provided as SEQ ID NO: 1.

The sequence of the new spirochete from New Jersey differed from that of the Texas tick in two locations, 1) base #345 of SEQ ID NO:1 is an A for the New Jersey tick, but a G for the Texas tick; this change does not alter the encoded amino acid; 2) base #591 of SEQ ID NO:1 is a G for the New Jersey tick, but an A for the Texas tick; this change also does not alter the amino acid sequence. Neither variation is near part of the flagellin gene where species-specific nucleotides are found or where species-specific amino acids are encoded. This variation may be considered an idiotype among this species.

The obtained nucleotide and deduced amino acid sequences were used to search by the BLAST algorithm the daily-updated sequence databases managed by the National Center for Biotechnology Information (Altschul et al., 1990). No identical matches were found to flagellin and rRNA genes of Borrelia spp.

The alignment of the deduced partial flagellin proteins of Amblyomma spirochete strains from Texas and New Jersey is shown in Table 5 with the comparable variable regions of the flagellin proteins of eight Borrelia spp.

TABLE 5

Alignment of variable regions of spirochete flagellin proteins, sequences in bold type have sequence identifiers as indicated[1].

```
              73*       80        90        100       110       120       130
AbTx_Fla†    LRVQVGANQDEAIAVNIFSTNVANLFGGEGV...QAAPAQEGAQQEGVQP......APAQGGISSPINVTTAIDAN
AbNJ_Fla     --------------------------------------------------------------------------
Bt_Fla       ---H-------------YAA------A---A----VS------------AAPAPAA-------VN--V---T----
Bp_Fla       ---H-------------YAS------A---A----VS------------AAPAPAA-------VN--V---TV---
Ba_Fla       ---H-------------YAA------A---A------------------ATPAPVA---P---VN----I---V---
Bh_Fla       ---H-------------YAS------A---A--------V--IG---EG-AAPAPAA-------VN-------V---
Bc_Fla       ---H-------------YAA------S---AQ---V-----------A-AAPAPAS-------VN--V----V---
Bz_Fla       ---H-------------YAA------A---AQAA----V-----E--A-Q-PTPAT--T----VN--V---TV---
Bg_Fla       ---H-------------YAA------S---AQAA-TA-V---------A-Q-PAPVT--S----VN--V---TV---
Bb_Fla       ---H-------------YAA------S---AQTA----V---V----A-Q-PAPAT--S----VN--V---TV---
```

[1]LRVQVGANQDEAIAVNIFSTNVANLFGGEGV; SEQ ID NO:15
QAAPAQEGAQQEGVQP; SEQ ID NO:16
APAQGGISSPINVTTAIDAN; SEQ ID NO:17
AAPAPAA; SEQ ID NO:18
ATPAPVA; SEQ ID NO:19
AAPAPAS; SEQ ID NO:20
AQAA; SEQ ID NO:21
PTPAT; SEQ ID NO:22
PAPVT; SEQ ID NO:23
AQTA; SEQ ID NO:24
PAPAT; SEQ ID NO:25
*Numbers correspond to amino acid positions of *B. lonestari* sp. nov. flagellin protein fragment of SEQ ID NO:2.
†Abbreviations and sources (accession numbers): Ab, *Amblyomma borrelia* strains from Texas and New Jersey; Bt, *B. turicatae* (M67462); Bp, *B. parkeri* (M67461); Ba, *B. anserina* (X75201); Bh, *B. hermsii* (A44894 and M67460); Bc, *B. crocidurae* (X75204); Bz, *B. afzelii*; Bg, *B.garnii* (X75203); Bb, *B. burgdorferi* (X69611 and P11089); and Fla, flagellin.

The flagellin proteins of these organisms differed from other borrelial flagellins at several positions and, uniquely among the Borrelia spp., lacked most of a proline-alanine-rich region beginning around nucleotide residue 119 of SEQ ID NO:2.

Phylogenetic classification was provided by distance matrix analysis and by comparison of 16S rRNA gene sequences (Table 6).

construct to provide a fusion protein for immunoassay. This construct supplies an N-terminus and a C-terminus for the recombinant fusion protein. The PMAL™ p2 expression vector, obtained from New England Biolabs, (Beverly, Mass.) and encoding the maltose binding protein, was used for this construct. The vector was digested with EcoRI and

TABLE 6

Signature base positions of 16S rRNA genes of Borrelia spp.[1]

| Base[2]: | 42 | 91 | 135 | 146 | 217 | 224 | 267 | 435 | 437 | 522 | 554 | 564 | 963 | 1074 | 1143 | 1215 |
|---|---|---|---|---|---|---|---|---|---|---|---|---|---|---|---|---|
| Base[3]: | 77 | 126 | 170 | 181 | 253 | 260 | 303 | 471 | 473 | 558 | 590 | 600 | 999 | 1110 | 1179 | 1251 |
| Ab_rna: | T | C | A | T | A | G | T | G | T | C | T | T | A | G | A | T |
| Bm_rna: | T | C | A | A | G | G | T | A | C | C | C | T | A | G | A | T |
| Bf_rna: | C | T | G | A | A | G | A | G | T | T | T | C | G | A | G | T |
| Bh_rna: | C | T | G | A | A | A | A | A | T | T | C | C | G | A | A | T |
| Ba_rna: | C | T | G | A | G | A | A | A | C | T | C | C | G | A | G | A |
| Bb_rna: | C | T | G | T | A | A | A | A | T | T | T | C | A | G | A | A |

[1]The GenBank accession number for the 16s rRNA gene sequence is U23211.
Abbreviations:
Ab, Amblyomma tick borrelia, Texas and New Jersey strains;
Bm, *B. miyamotae* sp. *nov.*;
Bf, Florida canine borrelia;
Bh, *B. hermsii*;
Ba, *B. anserina*;
Bb, *B. burgdorferi*.
Sources for sequences are given in legend for Table 5.
[2]Base position corresponding to SEQ ID NO: 3, the partial 16s rRNA sequence of *B. lonestari* sp. *nov*.
[3]Base positions correspond to positions of 16S rRNA gene of *B. burgdorferi*. Nine of the 16 positions are predicted to be in non-base paired regions of the 16S rRNA.

The 16S rRNA gene sequences of the Texas and New Jersey strains differed at only 2 out of 1336 nucleotide positions. Positions 733 and 739 have a T and G in those positions, respectively, in the Texas strain but a C and C in those positions, respectively, for the New Jersey strain. These residues are not considered to be species-specific nucleotides. A clone of the Texas strain designated pTxrna20, positioned in the vector pCRII™ and in the host *E. coli* strain INVαF' (Invitrogen), was deposited in the American Type Culture Collection, 12301 Parklawn Drive, Rockville, Md. 20852 as ATCC#. By distance matrix and parsimony analyses of the aligned sequences, the Amblyomma spirochetes represented a different species of Borrelia. The organism is in a group containing relapsing fever species. Parsimony analysis of base positions that were polymorphic in at least two of 6 species yielded a similar result (Table 6). Among the 6 sequences represented in Table 6, there were 49 aligned positions at which only one of the 6 species differed; 27 (53%) of these differences were in *B. burgdorferi*.

Other organisms in the relapsing fever group are the bird pathogen *B. anserina*, an unnamed organism recovered from the blood of two dogs in Florida, and a bacterium identified as *B. miyamotae* sp. nov. and isolated from *I. persulcatus* ticks in Japan (accession number D45192). By both distance matrix and parsimony analysis, *B. lonestari* sp. nov. is most closely related to *B. miyamotae* sp. nov., another Borrelia associated with hard rather than soft ticks. All Borrelia sp. identified to date infect vertebrates as well as arthropods (Barbour et al., 1986).

EXAMPLE 4

A Fusion Protein Comprising a Portion of *B. lonestari* sp. Nov. Flagellin

The present example describes the placement of the nucleotide sequence represented by SEQ ID NO:1 into a XbaI, ligated to the nucleic acid having SEQ ID NO:1, and having an in-frame stop codon and synthetic EcoRI and XbaI sequences added; and the recombinant molecule transfected into *E. coli* JM103. Methods for protein fusion and purification are described in the New England Biolabs brochure (1992). The resulting construct is represented by the partial sequence of SEQ ID NO:26. A fusion protein is made that, when cleaved with a blood protease factor Xa, releases flagellin protein having an additional Ile Ser Glu Phe (SEQ ID NO:27) sequence at the N-terminus and an additional Ala Val sequence at the C terminal end.

An antigen with minimal or no cross-reactivity with *B. burgdorferi* is desirable since the Lyme disease would be in the differential diagnosis. Therefore, a Borrelia gene encoding a flagellin protein, such as, Borrelia crocidurae, a relapsing fever agent of Eurasia, could provide the N- and C-terminal structure for the incorporation of the nucleotide sequence of the *B. lonestari* sp. nov. The resultant fused protein product, a recombinant, chimeric flagellin, would minimize cross-reactivity with antibodies to other Borrelia and spirochetes among patients samples in North America and would be a principal reagent in an ELISA test, Western blot assay or similar assay for antibodies to *B. lonestari* sp. nov. in patients and domestic animals suspected of harboring this agent. An advantage of a *B. lonestari* sp. nov. fusion protein having N- and C-terminal ends from another flagellin protein is that the fusion protein will more likely fold properly as a flagellin protein, its conformation will be more likely like that of the natural form, and it is expected to be easier to purify. The fusion protein may be purified according to Barbour et al., for example.

EXAMPLE 5

Restriction Fragment Length Polymorphisms for Assay of Specimens for Presence of *B. lonestari* sp. nov.

The present Example provides for analyses of the sequences provided in SEQ ID NOS:1 and 3 to indicate that different patterns of products are found when the *B. lonestari* sp. nov. DNA is cleaved by a restriction enzyme compared to the restriction patterns obtained from other species of Borrelia. This method allows for the identification not only of the new spirochete, but also of the other Borrelia species.

As shown in Example 2, an AluI digest of an about 330 bp PCR™ product (SEQ ID NO:4) and electrophoretic analysis of the enzyme digest yielded characteristic restriction fragments for different species of Borrelia, including *B. burgdorferi* B31, from two North American relapsing fever agents *B. hermsii* HS1 and *B. turicatae* "Ozonall", and from immunofluorescence-positive Amblyomma ticks from Texas and New Jersey. The gel patterns of the two Amblyomma tick samples revealed fragments of about 117, 85 and 55 base pairs; from *B. burgdorferi*, about 130 and 106 base pairs; from *B. hermsii*, about 160, 100 and 75 base pairs; and from *B. turicatae*, about 110 and 75 base pairs. Therefore, when appropriate size standards are included in an electrophoretic gel analysis, an approximation of the sizes and numbers of restriction fragments is sufficient to identify the Borrelia species.

Further enzyme digests that demonstrate polymorphisms are shown in Table 7. The data provided in Table 7 are for a PCR™ amplified product using PCR™ primers of SEQ ID NO. 11 and 12 or are from the whole gene (Ba, Bc, Bz).

TABLE 7

Restriction Fragment Length Polymorphisms for the Flagellin Gene of Various Borrelia Species[1]

|      | BlT | Bb  | Bh  | BlNJ | Ba  | Bc  | Bz  |
|------|-----|-----|-----|------|-----|-----|-----|
| AluI | 150 | 352 | 346 | 150  | 323 | 176 | 261 |
|      | 131 | 130 | 160 | 131  | 177 | 166 | 237 |
|      | 130 | 106 | 100 | 130  | 159 | 159 | 137 |
|      | 117 | 50  | 55  | 117  | 132 | 147 | 92  |
|      | 55  | 31  |     | 55   | 69  | 138 | 69  |
|      | 36  |     |     | 36   | 55  | 92  | 69  |
|      |     |     |     |      | 48  | 69  | 62  |
|      |     |     |     |      | 42  | 55  | 55  |
|      |     |     |     |      | 39  | 45  | 45  |
|      |     |     |     |      |     | 36  | 33  |
| NdeI | 540 | —   | 467 | 540  | 604 | 607 | —   |
|      | 101 |     | 101 | 101  | 508 | 508 |     |
|      |     |     | 90  |      |     |     |     |
| NheI | 511 | —   | —   | 511  | 604 | 945 | —   |
|      | 130 |     |     | 130  | 508 | 176 |     |
| DpnI | 384 | 407 | 460 | 384  | 373 | 357 | 489 |
|      | 180 | 180 | 131 | 180  | 281 | 284 | 287 |
|      | 77  | 77  | 67  | 77   | 226 | 226 | 226 |
|      |     |     |     |      | 121 | 117 | 121 |
|      |     |     |     |      | 111 | 81  |     |
|      |     |     |     |      |     | 40  |     |

[1]Sizes of fragments in base pairs are shown for each enzyme digest of a PCR ™ amplified product using SEQ ID NO: 11 and 12 as PCR ™ primers or from the whole gene (Ba, Bc, Bz). Fragments shorter than 30 base pairs are not listed.
Abbreviations and sources (accession numbers):
BlT, BlNJ *Borrelia lonestari* strains from Texas and New Jersey;
Bb, *B. burgdorferi* (X69611 and P11089);
Bh, *B. hermsii* (A44894 and M67460);
Ba, *B. anserina* (X75201);
Bc, *B. crocidurae* (X75204);
Bz, *B. afzelii*.

EXAMPLE 6

Method of Assaying a Clinical Sample

The present Example provides methods for the assay of a clinical sample for the determination of the presence or absence of *B. lonestari* sp. nov. A clinical sample may be a tick suspected of harboring the new Borrelia species, for example, or clinical samples obtained from a patient such as blood or serum samples, a skin biopsy, cerebrospinal fluid, or urine samples. A preferred sample is a blood or CSF sample for antibody or T cell assays. An immunoassay would be carried out on a patient sample of whole cells or sonicated cell extract, for example, using flagellin specific antiserum to test for the present of species-specific antigens. For nucleic acid assays, the nucleic acid, either RNA or DNA, would be amplified using a PCR™ reaction, for example, or an amplification procedure that would achieve a similar end, and the product analyzed as described herein. Reverse transcriptase may be used to make a cDNA copy of a messenger RNA molecule for amplification or ribosomal RNA may be obtained in a straightforward manner since it is abundant in the cell.

EXAMPLE 7

Vaccines for Protection Against *B. lonestari* sp. nov. Infection

The present inventors contemplate vaccines for use in both active and passive immunization embodiments. Immunogenic compositions, proposed to be suitable for use as a vaccine, may be prepared most readily directly from immunogenic *B. lonestari* sp. nov.-specific surface antigens, such as Vmp or Osp lipoprotein. Preferably, the antigenic material is purified by column chromatography, such as HPLC. The material may be dialyzed to remove undesired small molecular weight molecules and/or lyophilized for ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4.578,770, all incorporated herein by reference. Typically, such vaccines are prepared as injectables, either as liquid solutions or suspensions. Solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins or peptides may be formulated into the vaccine as neutral or salt forms. Pharmaceutically acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Altschul et al., *J. Mol. Biol.* 215, 403 (1990).
Barbour, Yale *J. Biol. Med.* 57, 521 (1984).
Barbour and Fish, *Science* 260, 1610 (1993).
Barbour and Hayes, *Microbiol. Rev.* 50, 381 (1986).
Barbour et al., *Infection and Immunity*, 52, 549 (1986).
Berland, et al., *Infect. Immun.* (United States), 59 (10) :3531–35 (1991).
Berland et al., *Infect. Immun.* 59, 3531 (1991).
Bloemer et al., *J. Med. Entomol.* 27, 543 (1990).
Centers for Disease Control and Prevention, *MMWR* 39, 397 (1989).
Centers for Disease Control and Prevention, *MMWR* 40, 417 (1991).
Cooney and Burgdorfer. *Am. J. Trop. Med. Hyg.* 23, 99 (1974).
Donnell, *Missouri Med* 89, 714 (1992).
Felsenstein, *Cladistics* 5, 164 (1989).
Felsenstein, PHYLIP (Phylogeny Inference Package) version 3.5c (Department of Genetics, University of Washington, Seattle, 1993).
Hair and Bowman, in *Morphology, Physiology, and Behavioral Biology of Ticks*, J. R. Sauer and J. A. Hair, Eds. (Ellis Horwood Ltd., Chichester, U.K., 1986), chap. 18.
K. Hansen et al., *J. Clin. Microbiol.* 26, 338 (1988).
Kocan et al., *J. Med. Entomol.* 29, 630 (1992).
Koch and Dunn, *Southwestern Entomologist* 5, 214 (1980).
Masters, *Postgrad. Med.* 94, 133 (1993).
Mather, T. N. and Mather, M. E., *J. Med. Entomol.* 27, 646 (1990).
Maupin et al., *5th International Conference of Lyme Borreliosis*, Arlington, Va. May 30 to Jun. 2, 1992, p. A259.
Maupin et al., *Am. J. Epidemiol.* 133, 1105 (1991).
Mukolwe et al., *J. Med. Entomol.* 29(4) :673:677 (1992).
Mukolwe et al., *J. Med. Entomol.* 29, 673 (1992).
Oliver et al., *Proc. Natl. Acad. Sci.*, U.S.A., 90(15):7371–7375, 1993.
Piesman and Sinsky, *J. Med. Entomol.* 25, 336 (1988).
Protein Fusion and Purification System, New England Biolabs Technical Brochure, 1992.
Relman, *J. Infect. Dis.* 168, 1 (1993).
Ryder et al., *J. Med. Entomol.* 29, 525 (1992).
Sambrook et al. (1989). Molecular cloning: A laboratory manual. Cold Spring Harbor Laboratory. Cold Spring Harbor, N.Y.
Sanger et al. *Proc. Natl. Acad. Sci.* USA 74:5463–5467 (1977).
Schulze et al., *Science* 224, 601 (1984).
Sigal and Curran, *Annu. Rev. Public Health* 12, 85 (1991).
U.S. Pat. No. 5,279,938—Rosa (1994).
W.P.I. Acc. No.: 92-041321/05—Barthhold, et al. (1992).
W.P.I. Acc. No.: 91-103941/15—Weisburg, W. G. (1991).

What is claimed is:

1. A purified nucleic acid segment encoding a polypeptide comprising the amino acid sequence of SEQ ID NO: 2, or its complement.

2. A purified nucleic acid segment comprising the nucleotide sequence of SEQ ID NO: 4 or SEQ ID NO: 26, or their complements.

3. The purified nucleic acid segment of claim 2, wherein the purified nucleic acid segment comprises the nucleotide sequence of SEQ ID NO: 4, or its complement.

4. The purified nucleic acid segment of claim 2, wherein the purified nucleic acid segment comprises the nucleotide sequence of SEQ ID NO: 26, or its complement.

* * * * *